(12) United States Patent
Gerlach et al.

(10) Patent No.: US 12,372,532 B2
(45) Date of Patent: Jul. 29, 2025

(54) METHOD FOR DETECTING A BINDING OF ANTIBODIES FROM A PATIENT SAMPLE TO DOUBLE-STRANDED DNA USING CRITHIDIA LUCILIAE CELLS AND FLUORESCENCE MICROSCOPY

(71) Applicant: EUROIMMUN Medizinische Labordiagnostika AG, Lübeck (DE)

(72) Inventors: Stefan Gerlach, Groß Groenau (DE); Jens Krauth, Lübeck (DE); Christian Marzahl, Erlangen (DE); Christopher Krause, Büchen (DE); Maick Danckwardt, Rondeshagen (DE); Melanie Hahn, Stockelsdorf (DE); Jörn Voigt, Lübeck (DE)

(73) Assignee: EUROIMMUN Medizinische Labordiagnostika AG, Lübeck (DE)

( * ) Notice: Subject to any disclaimer, the term of this patent is extended or adjusted under 35 U.S.C. 154(b) by 752 days.

(21) Appl. No.: 17/478,666

(22) Filed: Sep. 17, 2021

(65) Prior Publication Data

US 2022/0082567 A1    Mar. 17, 2022

(30) Foreign Application Priority Data

Sep. 17, 2020  (EP) ..................... 20196746

(51) Int. Cl.
*G01N 33/58* (2006.01)
*G01N 21/64* (2006.01)
(Continued)

(52) U.S. Cl.
CPC ....... *G01N 33/582* (2013.01); *G01N 21/6458* (2013.01); *G01N 21/6486* (2013.01);
(Continued)

(58) Field of Classification Search
CPC ........ G01N 33/582; G01N 3/045; G01N 3/08; G01N 1/6486; G01N 21/6458;
(Continued)

(56) References Cited

U.S. PATENT DOCUMENTS

2019/0030371 A1  1/2019  Han
2019/0371425 A1  12/2019  Kuo et al.
(Continued)

FOREIGN PATENT DOCUMENTS

WO    2018200715 A1    11/2018

OTHER PUBLICATIONS

Bayramoglu, Neslihan et al., Human Epithelial Type 2 Cell Classification with Convolutional Neural Networks, 2015 IEEE 15th International Conference on Bioinformatics and Bioengineering (BIBE), Nov. 2015, DOI:10.1109/BIBE.2015.7367705.
(Continued)

*Primary Examiner* — Kathryn Elizabeth Limbaugh
(74) *Attorney, Agent, or Firm* — Bochner PLLC; Andrew Bochner

(57) ABSTRACT

There is proposed a method for detecting a binding of autoantibodies from a patient sample to double-stranded deoxyribonucleic acid using *Crithidia luciliae* cells by means of fluorescence microscopy, including the steps of: provision of a substrate which has multiple *Crithidia luciliae* cells, incubation of the substrate with the patient sample which potentially has the autoantibodies, incubation of the substrate with secondary antibodies which have each been labelled with a preferably green fluorescent dye, acquisition of a fluorescence image of the substrate, identification by means of a first pretrained convolutional neural network of respective sub-images in the one fluorescence image that each represent a *Crithidia luciliae* cell, furthermore respective processing of at least one subset of the respective
(Continued)

sub-images by means of a second pretrained convolutional neural network for determining respective binding measures which indicate a respective extent of a binding of autoantibodies in a respective kinetoplast region of a respective *Crithidia luciliae* cell of a respective sub-image, and determination of an overall binding measure with regard to a binding of autoantibodies from the patient sample to double-stranded deoxyribonucleic acid on the basis of the respective binding measures.

14 Claims, 31 Drawing Sheets

(51) Int. Cl.
| | | |
|---|---|---|
| *G02B 21/00* | (2006.01) | |
| *G06N 3/045* | (2023.01) | |
| *G06T 7/00* | (2017.01) | |
| *G06T 7/90* | (2017.01) | |
| *G16B 40/00* | (2019.01) | |

(52) U.S. Cl.
CPC ....... *G02B 21/0076* (2013.01); *G02B 21/008* (2013.01); *G06N 3/045* (2023.01); *G06T 7/0012* (2013.01); *G06T 7/90* (2017.01); *G16B 40/00* (2019.02); *G01N 2800/104* (2013.01); *G06T 2207/10024* (2013.01); *G06T 2207/10056* (2013.01); *G06T 2207/10064* (2013.01); *G06T 2207/20021* (2013.01); *G06T 2207/20081* (2013.01); *G06T 2207/20084* (2013.01); *G06T 2207/30024* (2013.01)

(58) Field of Classification Search
CPC ... G01N 2800/104; G06T 7/90; G06T 7/0012; G06T 2207/10024; G06T 2207/10056; G06T 2207/10064; G06T 2207/20021; G06T 2207/20081; G06T 2207/20084; G06T 2207/30024; G06B 40/00; G02B 21/0076; G02B 21/008; G06V 20/29
See application file for complete search history.

(56) References Cited

U.S. PATENT DOCUMENTS

| | | |
|---|---|---|
| 2020/0011862 A1 | 1/2020 | Morgenroth et al. |
| 2020/0300764 A1 | 9/2020 | Gerlach et al. |
| 2021/0019883 A1 | 1/2021 | Krauth et al. |
| 2021/0245152 A1 | 8/2021 | Morgenroth et al. |

OTHER PUBLICATIONS

Gerlach, Stefan et al., Automated Evaluation of Crithidia luciliae Based Indirect Immunofluorescence Tests: A Novel Application of the EUROPattern-Suite Technology, Journal of immunology research, vol. 2015 (2015): 742402. doi:10.1155/2015/742402.

Gerlach, Stefan et al., Evaluation of Crithidia luciliae IFT can be reliably automated with EUROPattern, 31st Annual Meeting of the Association of Medical Laboratory Immunologists (AMLI), Aug. 2018.

Gerlach, Stefan et al., Evaluation of Crithidia luciliae IFT can be reliably automated with EUROPattern, 70th AACC Annual Scientific Meeting Abstracts, Jul. 31, 2018.

Lakos, Gabriella et al., Detection of anti-dsDNA antibodies by computer-aided automated immunofluorescence analysis, Journal of Immunological Methods, 433 (2016) 17-22, Jun. 2016.

Soda, Paolo et al., A decision support system for Crithidia Luciliae image classification, Artificial Intelligence in Medicine 51 (2011) 67-74, Jan. 2011.

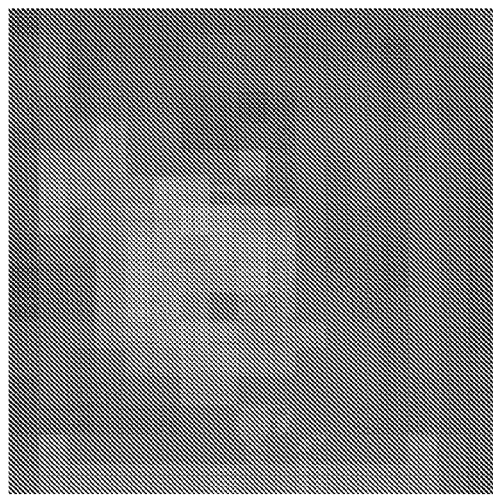
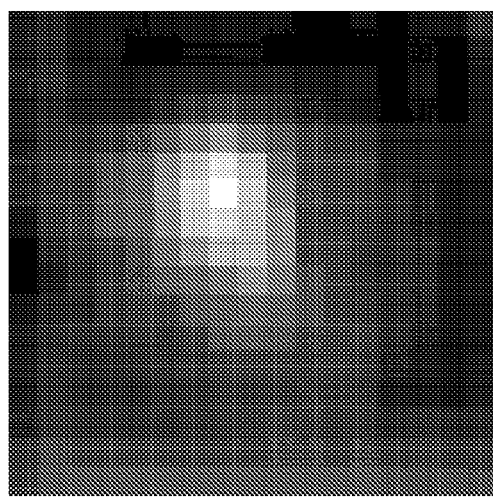
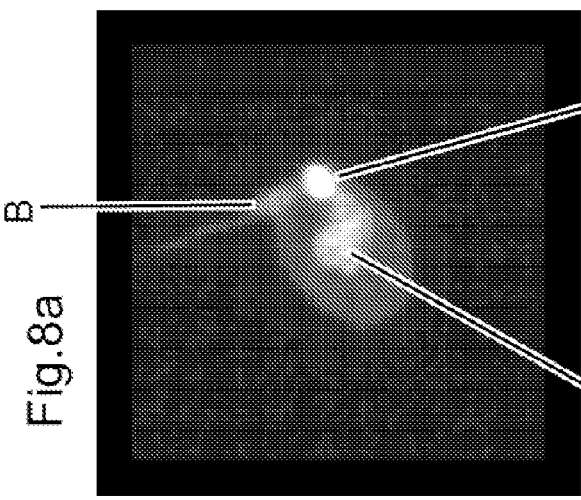

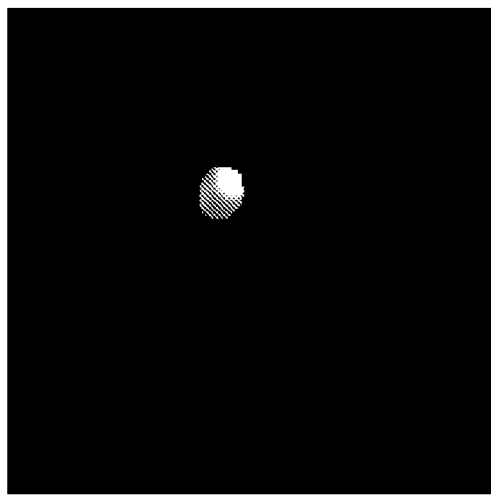
Fig.9c  SUB
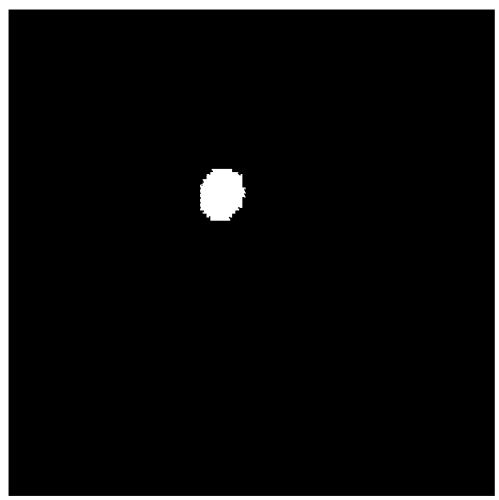
Fig.9b  BM
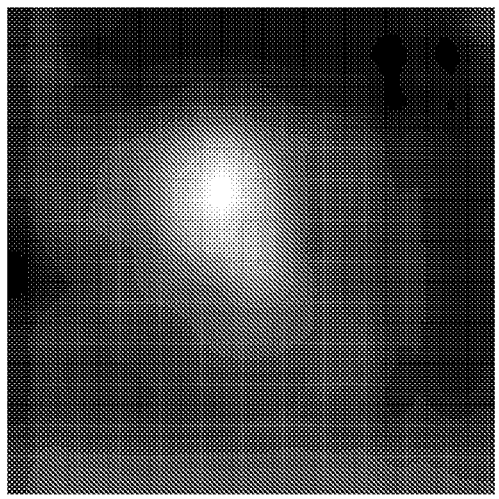
Fig.9a  VFM

METHOD FOR DETECTING A BINDING OF ANTIBODIES FROM A PATIENT SAMPLE TO DOUBLE-STRANDED DNA USING CRITHIDIA LUCILIAE CELLS AND FLUORESCENCE MICROSCOPY

CROSS-REFERENCE TO RELATED APPLICATIONS

The present application claims priority pursuant to 35 U.S.C. § 119(a) to EP patent application 20196746.0, filed Sep. 17, 2020, which is incorporated by reference herein in its entirety.

BACKGROUND

The invention relates to a method and a device for detecting a binding of autoantibodies from a patient sample to double-stranded deoxyribonucleic acid (DNA) using *Crithidia luciliae* cells by means of fluorescence microscopy and by means of digital image processing.

The detection of autoantibodies against deoxyribonucleic acids (DNA) is, for example, of crucial importance for the diagnosis of SLE (systemic lupus erythematosus). Here, a fundamental distinction must be made between two types: antibodies against dsDNA and antibodies against single-stranded, denatured DNA (ssDNA). Antibodies against dsDNA react with epitopes within the deoxyribose phosphate scaffold of DNA. By contrast, antibodies against ssDNA predominantly bind themselves to epitopes from the region of the purine and pyrimidine bases. However, they can also recognize epitopes of the deoxyribose phosphate scaffold. Anti-dsDNA antibodies are found almost exclusively in SLE. Their prevalence is 20% to 90% depending on the detection method and disease activity. Anti-dsDNA antibodies are sometimes also detected in patients with other autoimmune diseases and infections and, in rare cases, in clinically healthy individuals. The latter develop, in 85% of cases, an SLE within 5 years after the first anti-dsDNA detection. However, it is not possible to completely rule out an SLE if no antibodies against dsDNA are present. SLE is a systemic autoimmune disease from the group of connective tissue diseases. Diagnosis is guided by the 1997 update of the 11 criteria from the American College of Rheumatology (ACR). If 4 of the 11 criteria are present, it is possible to make the diagnosis of an SLE with 80% to 90% certainty.

An indirect immunofluorescence is an in vitro test for the determination of human antibodies against dsDNA. For example, so-called BIOCHIPs coated with *Crithidia luciliae* smears can serve as substrates. These are, for example, incubated with diluted patient samples. In the event of positive reactions, specific antibodies bind themselves to the antigens. In a further incubation step, bound antibodies (IgG) are, for example, stained with fluorescein-labelled anti-human antibodies and visualized under a fluorescence microscope.

Providing a substrate in which multiple *Crithidia luciliae* cells are fixed on the substrate is therefore known from the prior art. Such fixing can, for example, be effected by means of ethanol.

The substrate is then incubated with a patient sample, preferably diluted blood serum, the patient sample potentially having the autoantibodies to be detected. According to the prior art, the cells or the substrate can then be incubated with a so-called conjugate which has secondary antibodies labelled with a, for example, green fluorescent dye.

After irradiation of the incubated substrate with excitation light, a fluorescence radiation emitted by the green fluorescent dye can then be acquired as a fluorescence microscopy micrograph.

By way of example, such a micrograph is depicted in FIG. 1 as the image SG.

An individual *Crithidia* cell CR from FIG. 1 is depicted again in FIG. 2 in more detail. Such a sub-image TB of one *Crithidia luciliae* cell CR clearly shows a stain on the kinetoplast K, which is also referred to as a mitochondrion. There are further stains on the nucleus Z and on the basal body B.

For a reliable detection of a binding of autoantibodies from the patient sample to double-stranded DNA, it is crucial to detect a staining of multiple kinetoplasts in the fluorescence image SG of the substrate. As shown by FIG. 2, a binding or a staining may also be present for a nucleus Z and for a basal body B, meaning that the kinetoplast K must be reliably determined with respect to its position in the image by means of image processing.

By means of an evaluation with regard to a respective staining of respective kinetoplasts of respective *Crithidia luciliae* cells in the fluorescence image SG, it is then possible to ascertain altogether an averaged overall binding of autoantibodies from the patient sample to double-stranded DNA.

It is thus an object to provide a method using digital image processing for determining a binding of autoantibodies from a patient sample to double-stranded DNA, wherein a staining of different kinetoplast regions of different *Crithidia luciliae* cells within a fluorescence image can be reliably determined.

SUMMARY

There is proposed a method for detecting a binding of autoantibodies from a patient sample to double-stranded deoxyribonucleic acid using *Crithidia luciliae* cells by means of fluorescence microscopy and by means of digital image processing. The method comprises different steps. What takes place first of all is a provision of a substrate which has multiple *Crithidia luciliae* cells. What then takes place is an incubation of the substrate with the patient sample which potentially has the autoantibodies. Furthermore, what takes place is an incubation of the substrate with secondary antibodies which have each been labelled with a fluorescent dye which is preferably a green fluorescent dye. What takes place furthermore is an acquisition of a fluorescence image of the substrate in a color channel which corresponds to the fluorescent dye, wherein the color channel is preferably a green channel. What takes place furthermore is an identification of respective sub-images in the one fluorescence image which was acquired. The sub-images each represent a *Crithidia luciliae* cell. Said identification is done by means of a first pretrained convolutional neural network. What takes place furthermore is a respective processing of at least one subset of the respective sub-images by means of a second pretrained convolutional neural network for determining respective binding measures which indicate a respective extent of a binding of autoantibodies in a respective kinetoplast region of a respective *Crithidia luciliae* cell of a respective sub-image. Furthermore, what takes place is a determination of an overall binding measure with regard to a binding of autoantibodies from the patient sample to double-stranded deoxyribonucleic acid on the basis of the respective binding measures.

The patient sample is a liquid patient sample, preferably liquid blood or liquid blood constituents. More particularly, the liquid patient sample is liquid blood serum. Preferably, the patient sample has been diluted with so-called wash buffer, preferably so-called PBS Tween.

The conjugate may include secondary antibodies that have been labelled with the fluorescent dye.

The proposed method is especially a method for determining in vitro a presence of primary antibodies in a liquid patient sample.

The substrate is especially a biological sample which has animal-pathogenic hemoflagellates of the species *Crithidia luciliae*. These single-cell organisms have a double-stranded DNA-containing giant mitochondrion (kinetoplast) which has essentially none of the other antigens present in the nucleus. Primary autoantibodies from the patient sample that react with the kinetoplast are directed against dsDNA.

The fluorescence microscopy is especially a so-called indirect immunofluorescence microscopy (IIFT microscopy).

The substrate is preferably illuminated with excitation radiation in order to excite fluorescence radiation of the fluorescent dye. The excitation radiation is preferably a blue light and thus has wavelengths in a blue spectrum. The fluorescent dye is preferably a green fluorescent dye, especially of the type fluorescein isothiocyanate (FITC).

To elucidate one or more possibly achievable advantages of the method according to the invention, more detailed information is provided below.

BRIEF DESCRIPTION OF THE DRAWINGS

Without restricting the general concept of the invention, the invention is more particularly elucidated below on the basis of specific embodiments with reference to the figures, where:

FIG. 8a shows an exemplary sub-image, FIG. 8b shows a first final feature map, FIG. 8c shows a second final feature map to be preferably determined, FIG. 9a shows an interpolated version of the first final feature map from FIG. 8b, FIG. 9b shows a binary-value masking operator derived from the interpolated feature map from FIG. 9a, FIG. 9c shows a selected subordinate-image region of a subordinate image from the sub-image region from FIG. 8a, FIG. 10 shows steps for processing of the fluorescence image by means of the first convolutional neural network.

DETAILED DESCRIPTION

Figure 5:
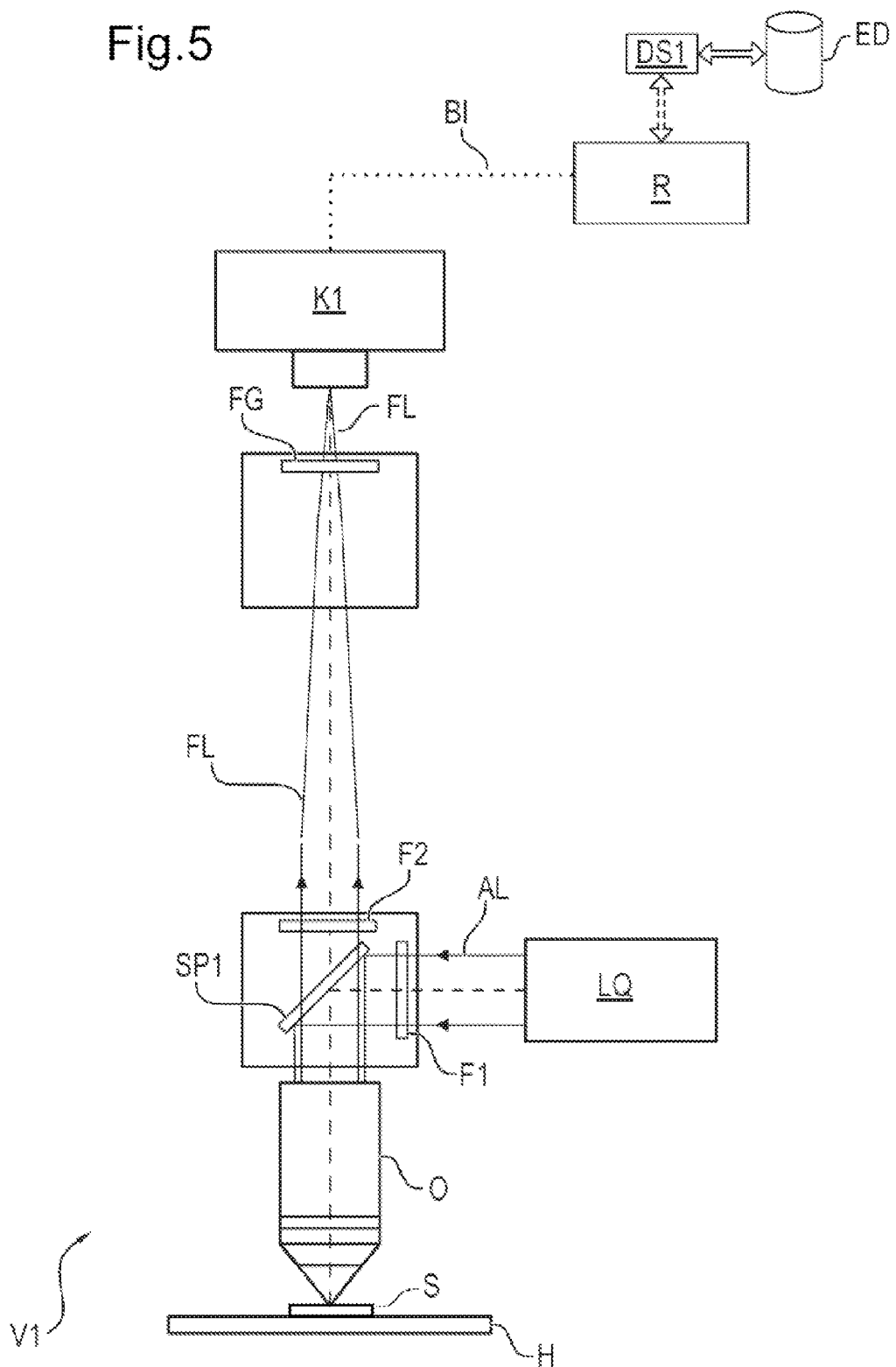
FIG. 5 shows an exemplary embodiment of a device according to the invention.

Referring to FIG. 5, a device V1 is shown, by means of which the method according to the invention can be carried out. The device V1 can be referred to as a fluorescence microscope. The device V1 comprises a mount H for a substrate S, which has been incubated in the manner described above. Via an optics unit O, excitation light AL from an excitation light source LQ is guided towards a substrate S. Resultant fluorescence radiation FL is then transmitted back through the optics unit O and passes through the dichroic mirror SP1 and an optional optical filter F2. Preferably, the fluorescence radiation FL passes through an optical filter FG which filters out a green channel. A camera K1 is preferably a monochrome camera which then, in the presence of an optical filter FG, acquires the fluorescence radiation FL in a green channel. According to an alternative embodiment, the camera K1 is a color camera which manages without use of the optical filter FG and acquires the fluorescence image in the corresponding color channel in the form of a green channel by means of a Bayer matrix. The camera K1 provides the image information item BI or the fluorescence image to a computing unit R, which processes said image information item BI.

Figure 1:
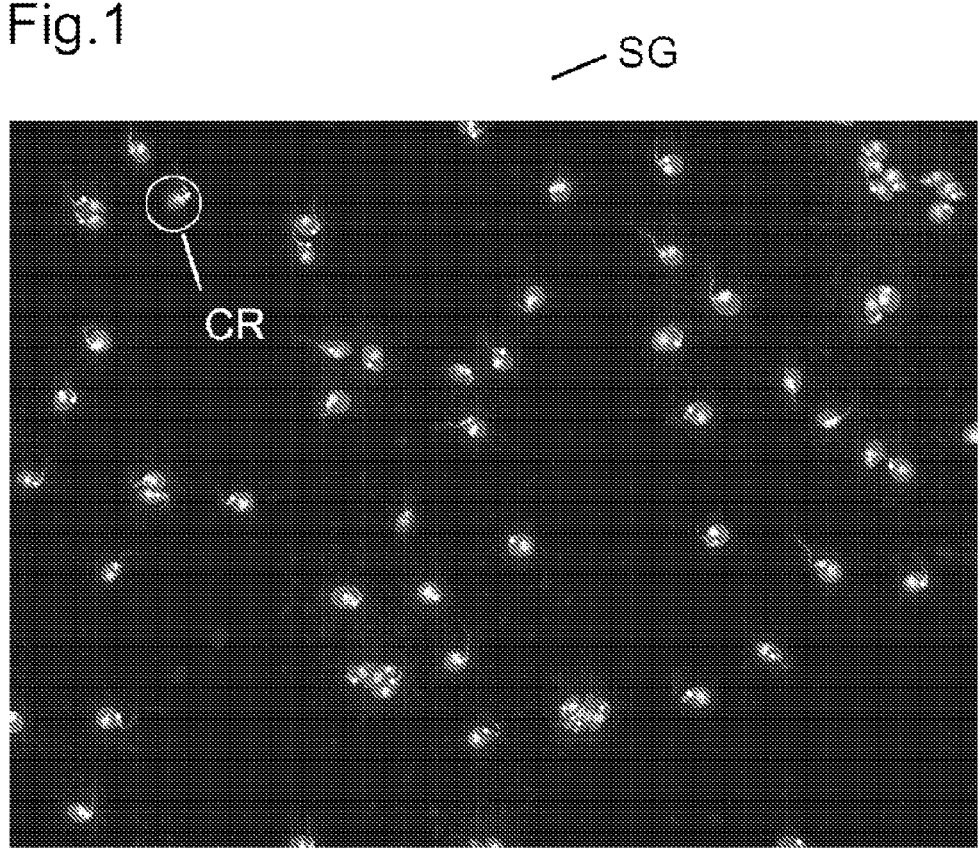
FIG. 1 shows a fluorescence image of a substrate having multiple *Crithidia luciliae* cells in the color channel.

FIG. 1 shows an exemplary fluorescence image SG in a green channel.

Figure 3:
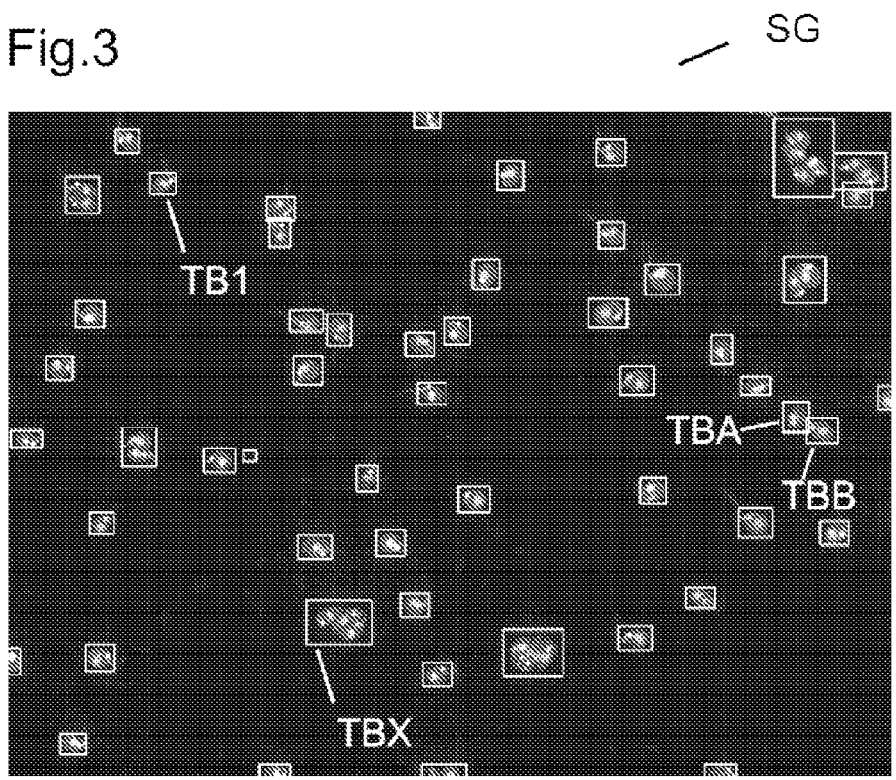
FIG. 3 shows the fluorescence image of the color channel with identified respective sub-image regions.

According to the invention, what are identified first of all, on the basis of the fluorescence image SG, are those sub-images which have especially at least one or at least a *Crithidia luciliae* cell. In relation to this, FIG. 3 shows corresponding rectangle-labelled sub-images, in particular sub-images TB1, TBA, TBB, TBX. A specific sub-image region TB1 is indicated in particular.

In the context of this application, a sub-image region can also be referred to as a sub-image.

Figure 2:
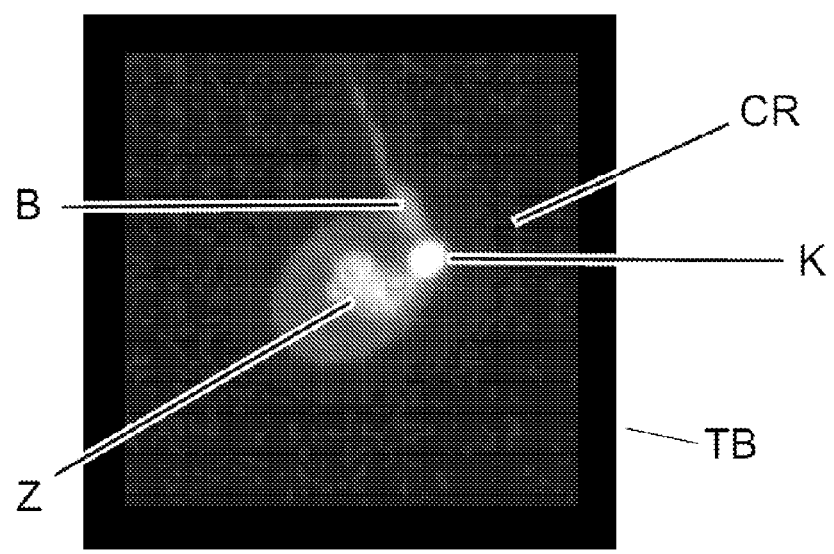
FIG. 2 shows a sub-image of the fluorescence image from FIG. 1 having one *Crithidia luciliae* cell.

Such an exemplary sub-image TB, which is the sub-image TB1 from FIG. 1, is depicted in FIG. 2. As can be seen in FIG. 2, there can be up to three significantly stained regions in a *Crithidia luciliae* cell owing to a binding of antibodies, specifically in the region of the kinetoplast K, the basal body B and the nucleus Z. Therefore, it must be ensured that, in the fluorescence image SG, any significant stainings are not used as assessment criterion, but only stainings of kinetoplast regions.

Figure 14A:
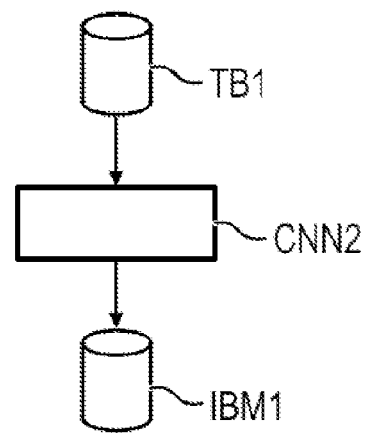
FIG. 14a shows a basic principle for ascertaining a binding measure of a binding of primary autoantibodies from the patient sample to a kinetoplast region for a sub-image region.

FIG. 14a shows a further step of the method according to the invention, in which, for a specific sub-image TB1, an associated binding measure IBM1 is determined by means of a second convolutional neural network CNN2. The binding measure IBM1 indicates an extent of a binding of autoantibodies in a kinetoplast region of the *Crithidia luciliae* cell depicted in the sub-image.

Figure 14B:
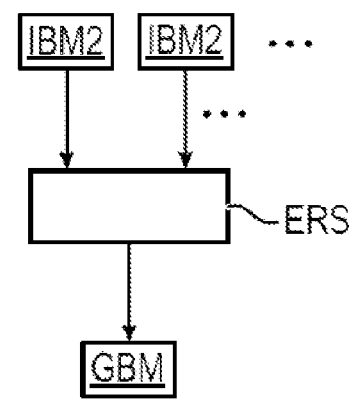
FIG. 14b shows a processing of multiple binding measures for determining an overall binding measure.

FIG. 14b illustrates a further step ERS of the method according to the invention, in which different respective binding measures IBM1, IBM2 of different respective sub-image regions are used as the basis to then ascertain an overall binding measure GBM with regard to the binding of autoantibodies from the patient sample to double-stranded DNA in the substrate that is to be detected.

Thus, the goal of the method according to the invention is a determination of the binding of the primary autoantibodies to the dsDNA in the respective kinetoplast regions of the respective *Crithidia luciliae* cells by means of determination of corresponding stainings of the corresponding kinetoplast regions by the fluorescent dye in the corresponding sub-image regions.

It should be stated that, in the method according to the invention, the entire fluorescence image SG from FIG. 1 is not simply supplied to an individual convolutional neural network for an entire identification of multiple stained kinetoplast regions, but that instead the invention explicitly deviates from such a total classification approach for the entire fluorescence image SG by means of a single convolutional neural network. Specifically, according to the invention, what takes place first of all is a pre-processing such that the sub-image regions or sub-images are identified in the fluorescence image by means of the first convolutional neural network. As can be seen in FIG. 2, there can be up to three significantly stained regions in a *Crithidia luciliae* cell owing to a binding of antibodies, specifically in the region of the kinetoplast K, the basal body B and the nucleus Z. The sub-images identified by the first convolutional neural network are then first each separately processed by the second convolutional neural network CNN2 in order to determine a respective subordinate image representing the kinetoplast region for a respective sub-image and in order to then especially determine, by means of the subordinate image, a respective binding measure indicating a respective extent of a binding of autoantibodies in a respective kinetoplast region of a respective *Crithidia luciliae* cell of a respective sub-image. In other words: said identified sub-image regions in particular are first each separately processed by the second convolutional neural network CNN2 in order to identify a respective subordinate image for a respective sub-image and in order to then determine, on the basis of the respective subordinate image, a respective binding measure for the respective sub-image. Such a binding measure indicates a respective extent of a binding of autoantibodies in a respective kinetoplast region of a respective *Crithidia luciliae* cell of a respective sub-image. These respective individual binding measures of the respective sub-images are used as the basis to then ascertain the overall binding measure.

According to the invention, what takes place is the identification of the sub-images in the one fluorescence image by means of the first pretrained convolutional neural network. This is advantageous because said first convolutional neural network is not used for the overall task of determining an overall binding measure with regard to the binding of autoantibodies from the patient sample to double-stranded deoxyribonucleic acid, but is merely used for the sub-task of identifying sub-images which each represent a *Crithidia luciliae* cell. Thus, said first convolutional neural network must only be pretrained in such a way that it identifies or localizes relevant sub-images in the fluorescence image. According to the invention, the identified sub-images are then each separately processed by the second convolutional neural network in order to ascertain for each of the sub-images an individual binding measure of a binding of autoantibodies to the respective kinetoplast regions of the respective *Crithidia luciliae* cell from the sub-image. Therefore, precisely the second convolutional neural network can be pretrained such that it focuses on the task of then identifying, or is configured to then identify, the kinetoplast region in a sub-image containing a particularly individual *Crithidia luciliae* cell. There is precisely no introduction of the entire image information of the fluorescence image into an individual convolutional neural network, but instead use of separate convolutional neural networks for the stated separate sub-tasks of identifying the sub-images and of determining the respective individual binding measures for the respective sub-images. As a result, these separate convolutional neural networks can be configured and pretrained such that they perform their respective tasks reliably, whereas configuring or training an individual convolutional neural network to process an entire fluorescence image for the purpose of determining the overall binding measure would require processing an extremely large amount of image information to serve the purpose of determining the overall binding measure, which is why then such an individual convolutional neural network would possibly be error-prone.

The proposed method is furthermore advantageous because, in the one fluorescence image of the one color channel, which is preferably a green channel, the first convolutional neural network directly identifies or localizes the sub-images in said one fluorescence image. Thus, it is therefore not necessary according to the invention that the substrate would have to be prepared with a so-called counterstain by means of another fluorescent dye such as, for example, Evans Blue to generate a red stain in a red channel; instead, such a counterstain for a red channel can simply be completely dispensed with according to the invention. This is achieved by the first convolutional neural network being configured or pretrained for the step or for the task of identifying the sub-images which each represent a *Crithidia luciliae* cell.

In other words: as a result of the approach described here, the method according to the invention achieves a high degree of accuracy in the localization of the kinetoplast regions and in a detection of a color change in the kinetoplast regions. If the entire fluorescence color image of the SG from FIG. 1 were to be supplied to a single convolutional neural network in order to detect a color change in a kinetoplast or in the various kinetoplast regions of the various *Crithidia luciliae* cells, other regions such as basal body regions or nucleus regions might be erroneously identified here as a kinetoplast region in each case and a determination of a binding of primary autoantibodies to dsDNA might therefore be distorted. Furthermore, a very large proportion of an entire fluorescence image SG of approx. 90% has merely background regions, meaning that, in the case of a processing of an entire fluorescence image SG by an individual CNN, the image pixels belonging to the background region would also have to be processed, which would make the individual CNN very complicated and a processing inefficient. Furthermore, from the entire fluorescence image SG, the individual CNN would also additionally have to identify those subordinate regions which each represent a kinetoplast, which is complicated owing to possible stainings of nucleus regions or basal body regions. Specifically, a staining of a kinetoplast region need not necessarily be present in the event of a staining of a basal body region and/or a nucleus region. Different positions of the *Crithidia luciliae* cells within the substrate or the fluorescence color image SG, as depicted in FIG. 1, mean that there are simply too many degrees of freedom for a reliable classification of individual image segments as kinetoplast by an individual convolutional neural network.

Instead of a processing of an entire fluorescence image by an individual CNN, what takes place separately according to the invention is a separate processing by the second convolutional neural network CNN2 for a respective sub-image. The position of the sub-image with regard to the entire fluorescence image is simply determined on the basis of an evaluation of the fluorescence image by means of the first convolutional neural network CNN1. What is made possible thereby is that the second convolutional neural network CNN2 can be explicitly trained on individual sub-images, i.e. on respective sub-images having an individual *Crithidia luciliae* cell. The second convolutional neural network CNN2 then only has to detect the position of the kinetoplast in this sub-image. Said position can simply be preferably determined as a so-called subordinate image. With regard to the individual kinetoplast, it is then possible to determine a binding measure for this cell or this kinetoplast by the second convolutional neural network CNN2.

In other words once again: according to the invention, what is made possible by supplying only determined individual sub-image regions in each case into the second convolutional neural network CNN2 is that the second convolutional neural network CNN2 is limited merely to an analysis of such a sub-image or an individual depiction of an individual *Crithidia luciliae* cell in order to identify the kinetoplast and to determine the binding measure with regard to the autoantibodies. If an entire fluorescence color image like the image SG from FIG. 1 were to be supplied to an individual convolutional neural network for a classification task for detecting different kinetoplasts in the course of a training phase, said individual convolutional neural network would have to be configured very greatly in terms of its degree of freedom and it would be very complicated and inefficient to train such an individual CNN. Since the second convolutional neural network CNN2 according to the invention has to process in each case only an individual sub-image region separately in order to then determine a corresponding binding measure, the second convolutional neural network CNN2 can be limited to a processing of an image representing a *Crithidia luciliae* cell, as depicted in FIG. 2 as image TB.

Advantageous embodiments of the invention are subject matter of the dependent claims and are more particularly elucidated in the following description with reference in some cases to the figures.

Preferably, the identification of the respective sub-images in the one fluorescence image is effected by assigning respective image segments of the fluorescence image to respective image segment classes from a group of image segment classes by means of the first pretrained convolutional neural network, wherein the group of the image segment classes comprises at least the following image segment classes: cell and background.

Preferably, the group of the image segment classes comprises at least the following image segment classes: cell, cell edge and background. Preferably, the class "cell" can also be referred to as class "cell body."

Preferably, the method comprises, for a respective sub-image, the steps of: selection of a respective subordinate image of the respective sub-image, wherein the respective subordinate image represents a respective kinetoplast region of a respective *Crithidia luciliae* cell, furthermore determination of the respective binding measure on the basis of the respective subordinate image. The method preferably comprises furthermore: determination of the overall binding measure on the basis of the respective binding measures.

Preferably, the method comprises the steps of: determination of at least one respective final feature map for a respective sub-image by means of the second convolutional neural network, furthermore determination of a respective confidence measure with regard to a presence of a binding of autoantibodies in a respective kinetoplast region for the respective sub-image or for a respective final feature map, especially on the basis of the respective final feature map, furthermore selection of a subset of the sub-images or selection of a subset of the respective final feature maps on the basis of the determined confidence measures, furthermore respective processing of the respective feature maps of the respective selected sub-images for determining the respective binding measures. The method preferably comprises furthermore: determination of the overall binding measure on the basis of the respective binding measures.

Preferably, the method comprises, for a respective sub-image from the selected subset, the steps of: selection of a respective subordinate image of the respective sub-image on the basis of the respective final feature map corresponding to the respective sub-image, wherein the respective subordinate image represents a respective kinetoplast region of a respective *Crithidia luciliae* cell, and furthermore determination of the respective binding measure on the basis of the respective subordinate image. The method preferably comprises furthermore: determination of the overall binding measure on the basis of the respective binding measures.

Preferably, the method comprises, for a respective sub-image from the selected subset, furthermore the steps of: ascertainment of a respective masking operator on the basis of the respective final feature map, furthermore selection of the respective subordinate image of the respective sub-image by means of application of the respective masking operator to the respective sub-image, furthermore determination of the respective binding measure on the basis of the respective subordinate image. The method preferably comprises furthermore: determination of the overall binding measure on the basis of the respective binding measures.

Preferably, the method is configured such that, in the course of a processing of a sub-image, the second convolutional neural network, in a first processing level, generates a first set of resultant feature maps on the basis of the sub-image by means of a first convolutional layer, furthermore in a second processing level, generates a second set of resultant feature maps on the basis of the first set of two-dimensional feature maps by means of a second convolutional layer and furthermore generates a third set of resultant feature maps on the basis of the second set of two-dimensional feature maps by means of a third convolutional layer, wherein the second set has a smaller number of resultant feature maps than the first set and the third set has a larger number of resultant feature maps than the second set.

Preferably, the method is configured such that the second convolutional layer and the third convolutional layer are in a sequence as sub-steps of a sequential processing path, wherein, in the second processing level, there is in parallel to the sequential processing path a further processing path in which the second convolutional neural network generates a fourth set of resultant feature maps on the basis of the first set of two-dimensional feature maps by means of at least one fourth convolutional layer, wherein, furthermore, the second convolutional neural network generates on the basis of the third and the fourth set of resultant feature maps the final feature map corresponding to the sub-image and wherein, furthermore, the number of successive convolutional layers in the parallel processing path is smaller than the number of successive convolutional layers in the sequential processing path.

Preferably, the method comprises the steps of: acquisition of a first preliminary fluorescence image using a predefined acquisition parameter, establishment of whether a brightness of the first preliminary fluorescence image exceeds a maximum brightness, in the event of the first preliminary fluorescence image not exceeding the maximum brightness, use of the first preliminary fluorescence image as the fluorescence image, in the event of the first preliminary fluorescence image exceeding the maximum brightness, acquisition of a second preliminary fluorescence image and use of the second preliminary fluorescence image as the fluorescence image.

There is furthermore proposed a device according to the invention for detecting a binding of autoantibodies from a patient sample to double-stranded deoxyribonucleic acid using *Crithidia luciliae* cells by means of fluorescence microscopy and by means of digital image processing, comprising a mounting device for a substrate which has multiple *Crithidia luciliae* cells and which has been incubated with a patient sample having the autoantibodies and, furthermore, with secondary antibodies which have each been labelled with a fluorescent dye. The device comprises furthermore at least one image acquisition unit for acquiring a fluorescence image of the substrate. The device comprises furthermore at least one computing unit which is designed to identify by means of a first pretrained convolutional neural network respective sub-images in the one fluorescence image that each represent at least one *Crithidia luciliae* cell, furthermore to respectively separately process at least one subset of the respective sub-images by means of a pretrained second convolutional neural network for determining respective binding measures which indicate a respective extent of a binding of autoantibodies in a respective kinetoplast region of a respective *Crithidia luciliae* cell of a respective sub-image, and furthermore to determine an overall binding measure of a binding of autoantibodies from the patient sample to double-stranded deoxyribonucleic acid on the basis of the respective binding measures.

There is furthermore proposed a computing unit which is designed, in the course of a digital image processing, to receive a fluorescence image which represents a staining of a substrate, which in turn has multiple *Crithidia luciliae* cells, by a fluorescent dye, furthermore to identify by means of a first convolutional neural network respective sub-images in the fluorescence image that each represent at least one *Crithidia luciliae* cell, furthermore to respectively separately process at least one subset of the respective sub-images by means of a pretrained second convolutional neural network for determining respective binding measures which indicate a respective extent of a binding of autoantibodies in a respective kinetoplast region of a respective *Crithidia luciliae* cell of a respective sub-image, and furthermore to determine an overall binding measure of a binding of autoantibodies from the patient sample to double-stranded deoxyribonucleic acid on the basis of the respective binding measures.

There is furthermore proposed a data network device comprising at least one data interface for receiving a fluorescence image which represents a staining of a substrate, which in turn has multiple *Crithidia luciliae* cells, by a fluorescent dye. The data network device comprises furthermore a computing unit which is designed, in the course of a digital image processing, to identify by means of a first convolutional neural network respective sub-images in the one fluorescence image that each represent at least one *Crithidia luciliae* cell, furthermore to respectively separately process at least one subset of the respective sub-images by means of a pretrained second convolutional neural network for determining respective binding measures which indicate a respective extent of a binding of autoantibodies in a respective kinetoplast region of a respective *Crithidia luciliae* cell of a respective sub-image, and furthermore to determine an overall binding measure of a binding of autoantibodies from the patient sample to double-stranded deoxyribonucleic acid on the basis of the respective binding measures.

There is furthermore proposed a method for digital image processing, comprising the steps of: receiving of a fluorescence image which represents a staining of a substrate, which in turn has multiple *Crithidia luciliae* cells, by a fluorescent dye, furthermore identification by means of a first convolutional neural network of respective sub-images in the fluorescence image that each represent at least one *Crithidia luciliae* cell, furthermore respective separate processing of at least one subset of the respective sub-images by means of a pretrained second convolutional neural network for determining respective binding measures which indicate a respective extent of a binding of autoantibodies in a respective kinetoplast region of a respective *Crithidia luciliae* cell of a respective sub-image, and furthermore determination of an overall binding measure of a binding of autoantibodies from the patient sample to double-stranded deoxyribonucleic acid on the basis of the respective binding measures.

There is furthermore proposed a computer program product comprising commands which, upon execution of the program by a computer, prompt said computer to carry out the method according to the invention for digital image processing.

There is furthermore proposed a data carrier signal which transmits the proposed computer program product.

Figure 13:
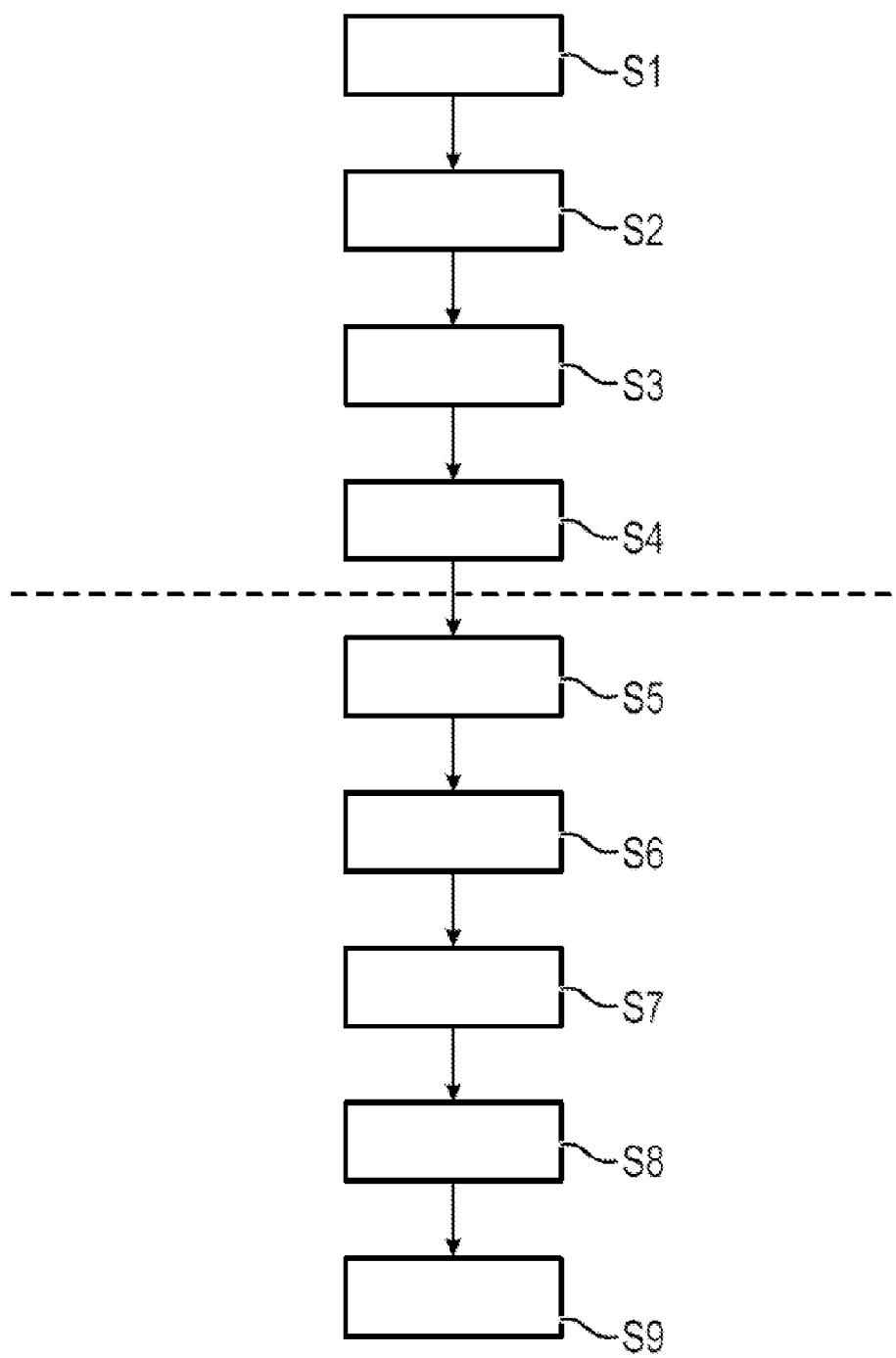
FIG. 13 shows steps for carrying out the method according to the invention.

FIG. 13 illustrates different steps for carrying out the method according to the invention. In a step S1, a substrate which has multiple *Crithidia luciliae* cells is provided. In a step S2, the substrate is incubated with the patient sample. The patient sample potentially has the autoantibodies. In a joint step S3 and S4, the substrate is incubated with secondary antibodies which have each been labelled with a preferably green fluorescent dye. In a step S5, what takes place is an acquisition of a fluorescence image of the substrate in a color channel which is preferably a green channel and which corresponds to the fluorescent dye. In a step S6, what takes place is an identification by means of a first pretrained convolutional neural network of respective sub-images in the one fluorescence image that each represent a *Crithidia luciliae* cell.

In a step S7, what takes place is a respective processing of at least one subset of the respective sub-images by means of a pretrained second convolutional neural network for determining respective binding measures which indicate a respective extent of a binding of autoantibodies in a respective kinetoplast region of a respective *Crithidia luciliae* cell of a respective sub-image. In a step S8, what takes place is a determination of an overall binding measure with regard to the binding of autoantibodies from the patient sample to double-stranded DNA in the substrate on the basis of the respective binding measures of the respective sub-images. In a step S9, what preferably takes place is a provision of the overall binding measure and what alternatively or additionally takes place is an outputting and/or displaying of the overall binding measure.

FIG. 14a shows an exemplary separate processing of an individual sub-image region TB1 by a second convolutional neural network CNN2 for determining an individual binding measure IBM1. The binding measure IBM1 indicates an individual extent of a binding of autoantibodies in an individual kinetoplast region of an individual *Crithidia luciliae* cell of the individual sub-image region TB1.

FIG. 14b illustrates a determination of the overall binding measure GBM by an ascertainment step ERS, which corresponds to the step S8 from FIG. 13, for determining the overall binding measure GBM on the basis of respective binding measures IBM1, IBM2 of respective sub-images.

FIG. 5 illustrates an exemplary embodiment of the device V1 according to the invention. The device V1 comprises a mounting device H for the substrate S. Excitation light AL from an excitation light source LQ is prefiltered via an optical filter F1 and then guided through an optics unit O by means of a dichroic mirror SP1 towards the substrate. Resultant fluorescence radiation or resultant fluorescence light FL then passes from the substrate back through the objective O through the dichroic mirror SP1 and through a final filter F2. The optical filter F2 filters out a wavelength of the excitation radiation or the excitation light AL. The fluorescence light FL is then supplied to at least one image acquisition unit in the form of a camera K1. Via an optical filter FG to be preferably used, the fluorescence light FL is filtered in a color channel such that the fluorescence light FL represents a so-called green channel after passage through the filter FG. In this case, the image acquisition unit K1 is preferably a monochrome camera. In an alternative embodiment, the optical filter FG is not present and the camera K1 is a color camera which filters out a green image or a green color channel image using, for example, a Bayer matrix and acquires the fluorescence image as a preferably green image. Via a data interface DS1, the device V1 can provide result data ED which indicate the overall binding measure.

A computing unit R is designed to receive the fluorescence image in the form of digital data BI. The computing unit R is furthermore designed to carry out the steps S5 to S9 of the method according to the invention.

Figure 20:
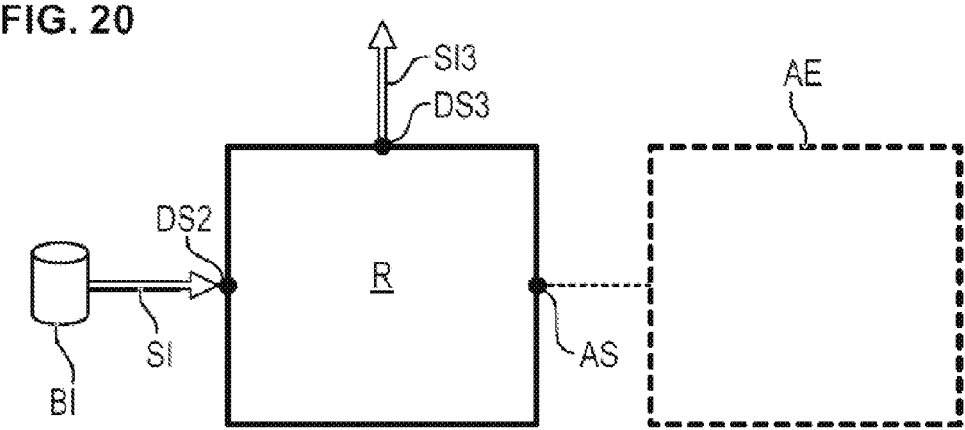
FIG. 20 shows an exemplary depiction of a computing unit according to the invention.

A computing unit R according to the invention can also be realized as depicted in FIG. 20. Here, the computing unit R receives the fluorescence image via at least one data interface DS2 in the form of at least one data signal SI. After carrying out the relevant steps S5 to S8 of the method according to the invention from FIG. 13, the computing unit R has determined the overall binding measure of the binding of autoantibodies from the patient sample to double-stranded DNA. Preferably, the computing unit R comprises an output interface AS in relation to a display unit AE, via which the overall binding measure can be output or displayed. Preferably, the computing unit R comprises a further data interface DS3 towards a data network, via which data interface the computing unit provides the overall binding measure via a data signal SI3. The data interfaces DS2, DS3 of the computing unit R can also be a common data interface. The data interfaces DS2, DS3 are preferably network data interfaces.

Figure 21:
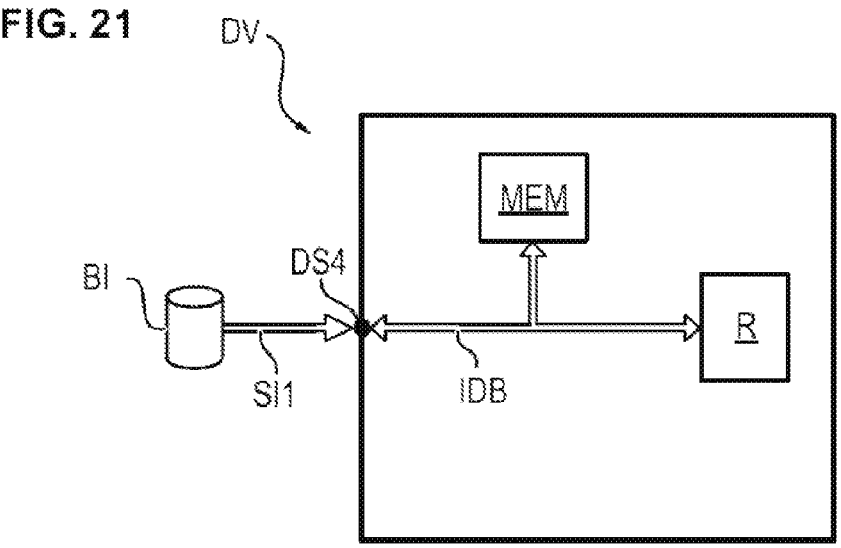
FIG. 21 shows an exemplary depiction of a data network device according to the invention.

The computing unit R can also be part of a data network device DV according to the invention, as illustrated in FIG. 21. The data network device DV comprises at least one data interface DS4 for receiving the fluorescence image BI by means of at least one data signal SI1. The data network device DV comprises the computing unit R, which is preferably connected to a storage unit MEM and the data interface DS4 via an internal data bus IDB. The computing unit R is designed in that manner as previously described with regard to FIG. 20. The data network device DV can be an individual computer or else a so-called cloud solution. The data network device DV thus carries out, by means of the computing unit R, a method according to the invention for digital image processing, in which method the fluorescence image BI is received and in which method the computing unit R carries out the steps S5 to S8 from FIG. 13.

Figure 22:
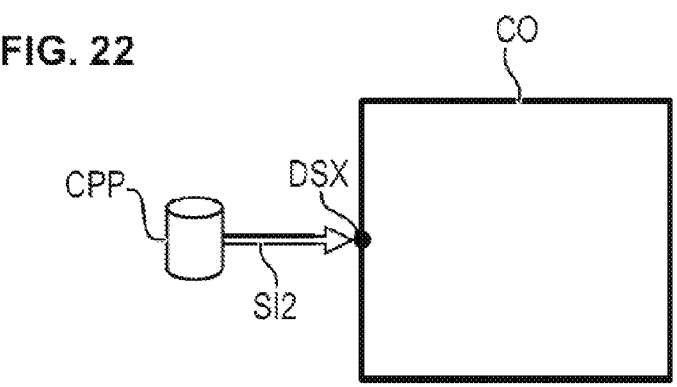
FIG. 22 shows an exemplary depiction of a computer program product according to the invention and of a data carrier signal according to the invention.

FIG. 22 illustrates a computer program product CPP according to the invention, which comprises commands which, upon execution of the program by a computer CO, prompt said computer to carry out a digital image-processing method according to the invention.

The computer program product CPP can be provided in the form of a data carrier signal S12 and be received by a computer CO by means of a data interface DSX situated on the computer CO. The data carrier signal S12 thus transmits the computer program product CPP.

Figure 4:
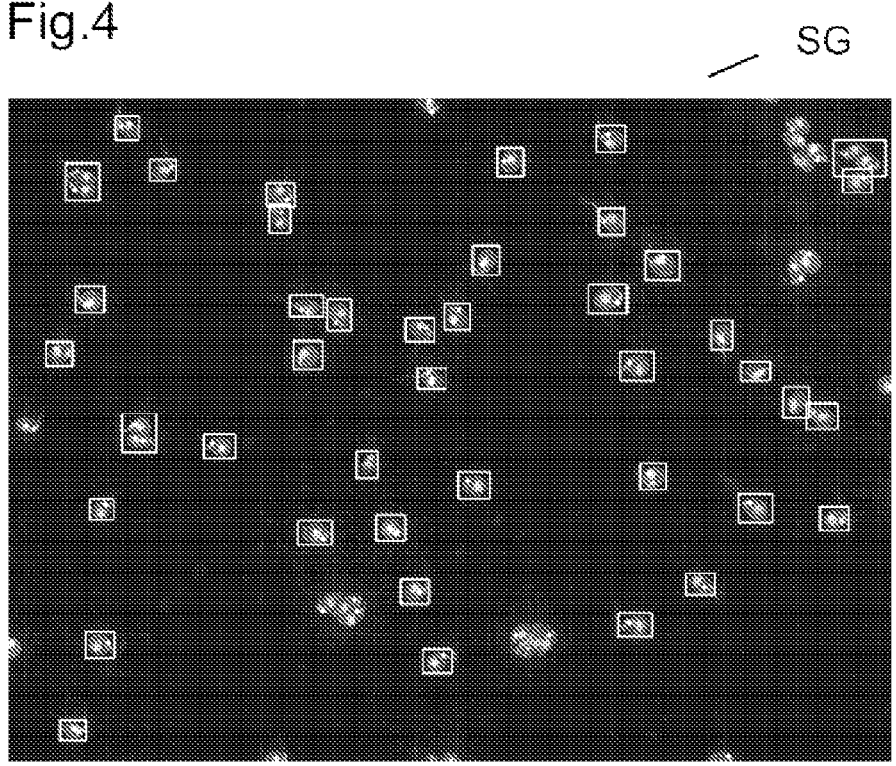
FIG. 4 shows the fluorescence image with an indication of selected sub-images from the total set of sub-images from FIG. 3.
Figure 15:
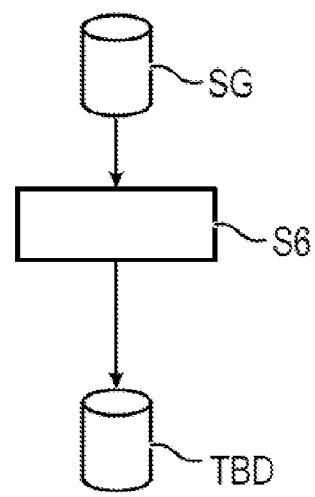
FIG. 15 shows steps for determining sub-image regions in the fluorescence color image of the color channel.

FIG. 15 illustrates the processing of the fluorescence image SG in the step S6 for obtaining the sub-image data TBD, which represent or indicate the sub-images. FIG. 3 shows the fluorescence image SG with indicated sub-images TB1, TBA, TBB, TBX, which are recorded in the fluorescence image SG by means of respective rectangles. Further sub-images which have not been named are recorded in the fluorescence image SG by means of further rectangles. FIG. 4 shows the fluorescence image SG with specifically selected sub-images. For example, the sub-image TBX from FIG. 3 is not one which was selected for determining a subset of sub-images, since said sub-image TBX from FIG. 3 is no longer indicated in FIG. 4. This step of selecting a subset of sub-images will be explained in detail later.

Figure 10:
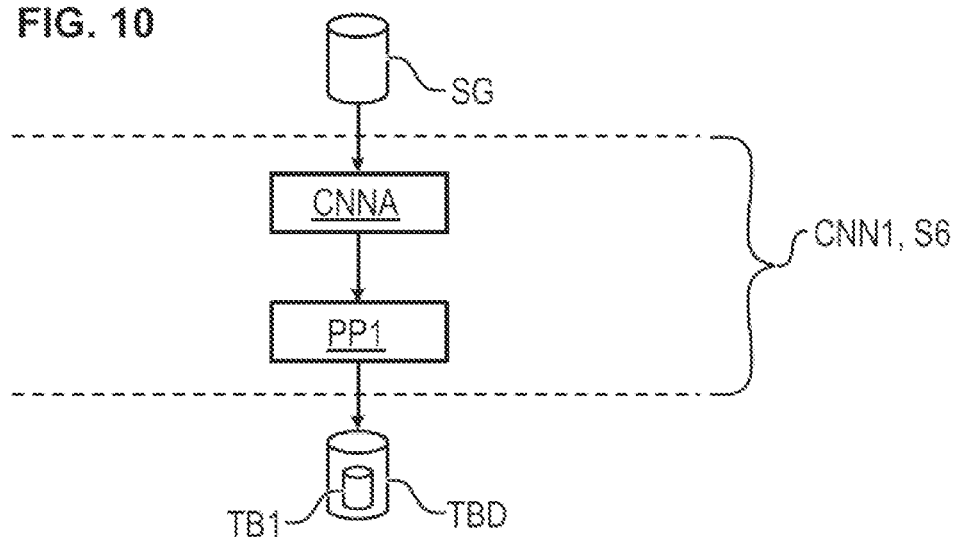

The step S6 depicted in FIG. 15 is explained in detail in FIG. 10. The step S6 is carried out by the first convolutional neural network CNN1, which preferably comprises a convolutional neural network CNNA and a so-called postprocessing PP1 as respective sub-steps. The sub-image data TBD ascertained by means of the first pretrained convolutional neural network CNN1 then comprise the identified sub-images such as, for example, the sub-image TB1 or indicate said sub-images.

Figure 11:
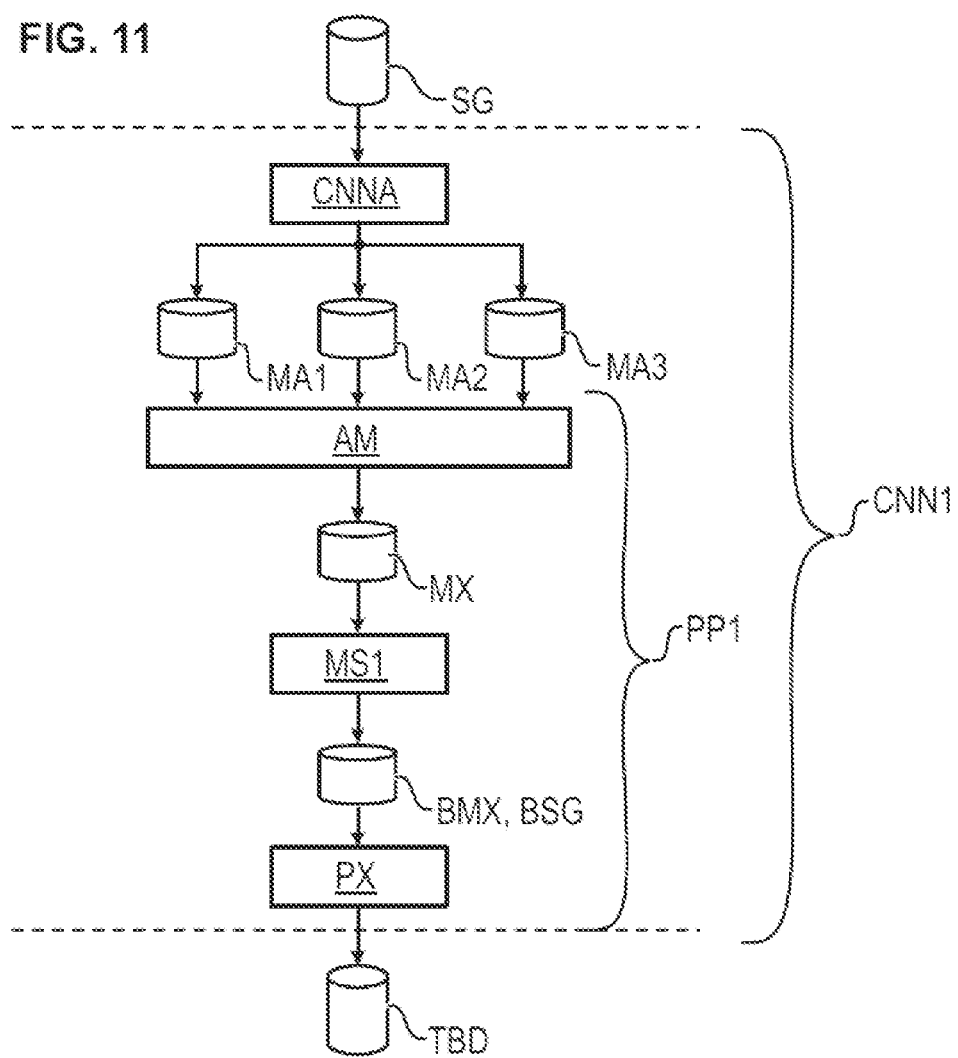
FIG. 11 shows detailed steps from the processing by the first convolutional neural network.

FIG. 11 shows further details about the first convolutional neural network CNN1.

The convolutional neural network CNNA used in the first convolutional neural network CNN1 as first sub-step will be explained in detail later with reference to FIGS. 30 to 33.

Said convolutional neural network CNNA receives the fluorescence image SG and assigns these respective image segments or these respective pixels of the fluorescence image SG to respective image segment classes. Said image segment classes form a group of image segment classes which comprise at least the image segment classes cell and background. Preferably, said group of the image segment classes comprises the image segment classes cell, cell edge and background.

The fluorescence image SG can be understood as an information item $$SG(m), m=1 \ldots M, M=1048576$$

in which the index m is the pixel index or the image segment index and in which a resolution of 1024×1024 results in the parameter M having the value M=1048576. A person skilled in the art knows that selection of a different image resolution for the fluorescence image SG yields a different value for the parameter M. The fluorescence image can also be scaled down.

The convolutional neural network CNNA then ascertains respective matrices or maps MA1, MA2, MA3 for the respective image segment classes. A map or a matrix MA1, MA2, MA3 for preferably K=3 image segment classes can thus be written as:

$$MAk, k=1 \ldots K$$

The resolution of a map is preferably of identical resolution to that of the fluorescence image SG, and so:

$$MAk(m), m=1 \ldots M$$

where preferably M=1048567.

Figure 12A:
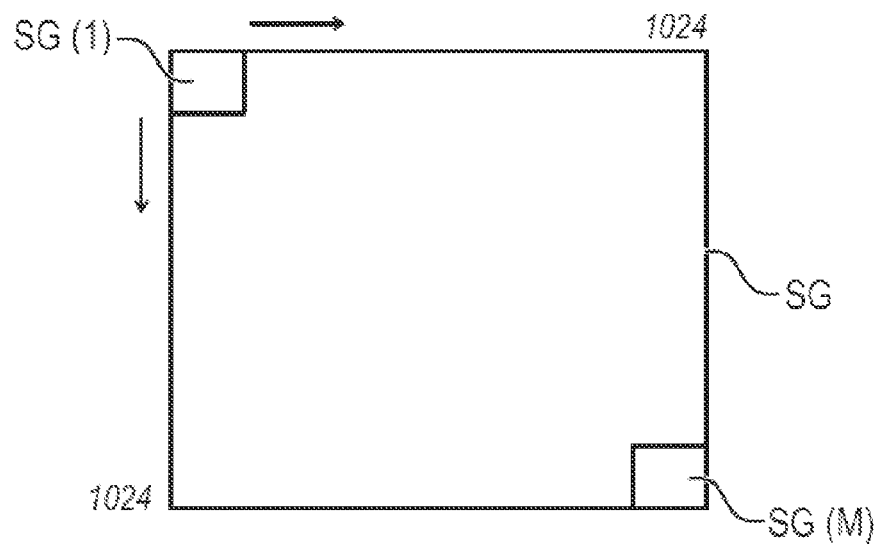
FIG. 12a shows an exemplary depiction of the fluorescence image.

In relation to this, FIG. 12a shows an exemplary depiction of the fluorescence image SG with an indication of the first pixel SG (1) and of the last pixel SG (M).

Figure 12B:
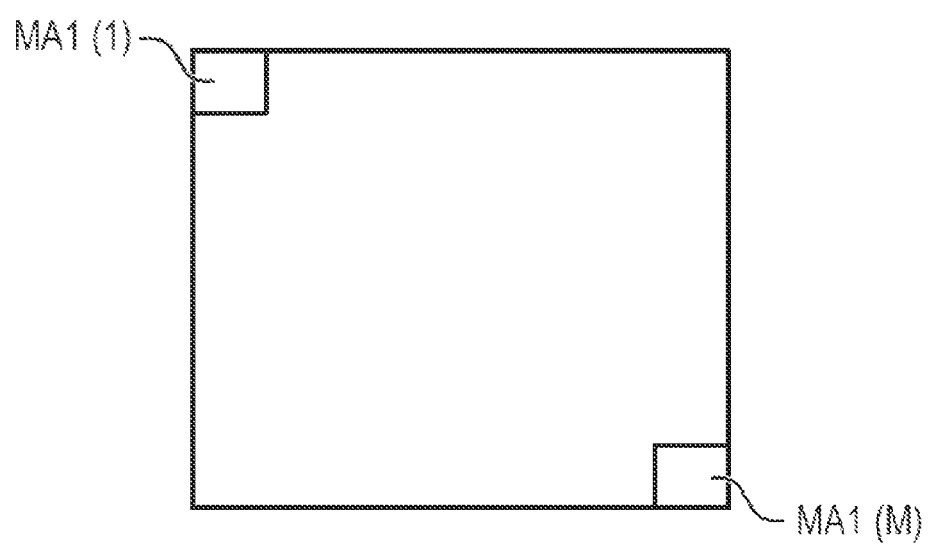
FIG. 12b shows an exemplary depiction of a first classification matrix or a first classification map.

In relation to this, FIG. 12b then shows the map or matrix MA1 of the first image segment class in a corresponding manner. Relevant corresponding maps or matrices MA2, MA3 can then be set up for the other image segment classes.

In an individual entry MA1 (1), the map MA1 then has a confidence measure which indicates that the corresponding image segment or the pixel SG (1) belongs to the first image segment class of the map or the matrix MA1.

Accordingly, this can be set up for the maps or matrices MA2, MA3 of the relevant second or third image segment class.

The maps or matrices MA1, MA2, MA3 also depicted in FIG. 11 are then, in a further step AM, subjected to a so-called argmax operation, which then ascertains for a respective image segment or a respective pixel from the fluorescence image SG the image segment class to which said pixel or said image segment most likely belongs.

This is done by forming a classification matrix MX where:

$$MX(m), m=1 \ldots M$$

For determination of the classification matrix MX, the argmax operation is then executed according to:

$$MX(m) = \underset{k}{\operatorname{argmax}} \{MAk(m), \ldots, MAK(m)\}$$

The values of the classification matrix MX or an individual value MX(m) is then from the set {1, 2, 3}, wherein, for example, a 1 indicates that the corresponding image segment or the corresponding pixel from the fluorescence image SG belongs to the class background. The value 2 indicates, for example, that the corresponding pixel or the corresponding image segment from the fluorescence image SG belongs to a cell edge. Preferably, the value 3 indicates that the corresponding pixel or the corresponding image segment from the fluorescence image belongs to the class cell or cell body.

Figure 6:
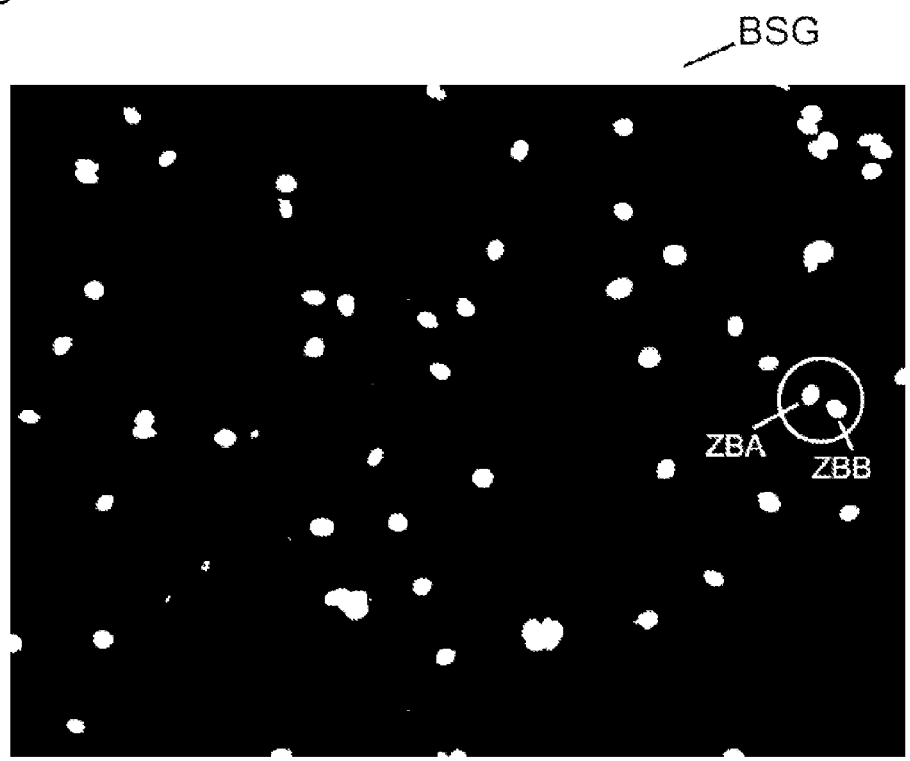
FIG. 6 shows a binary image ascertained for the fluorescence image, as a binary information item or binary mask.

What then additionally preferably takes place is a so-called mapping step MS1, which transfers the classification matrix MX to a binary classification matrix BMX, which can also be understood as a binary image information item BSG. Such a result of a binary image information item BSG is depicted in FIG. 6. Such a binary image information item BSG or BMX can also be written as $$BMX(m), m=1 \ldots M$$

The mapping in the mapping step MS1 is then preferably effected such that all those image segments or pixels having index m from the matrix MX that are assigned to the background, i.e. belong to class 1, are then also assigned to the background in the binary matrix BMX final and are set to the value 0. All those image segments or pixels which were assigned to the cell edge in the matrix MX, i.e. belong to class 2, are also assigned to the background in the binary matrix BMX final and set to the value 0. All those image segments or pixels which were assigned to the cell or the cell body in the matrix MX, i.e. belong to class 3, are assigned as cell region in the binary matrix BMX final and set to the value 1. This is done according to the rule:

$$BMX(m) = \begin{cases} 0 \text{ for } MX(m) = 1 \vee 2 \\ 1 \text{ for } MX(m) = 3 \end{cases}$$

Figure 7A:
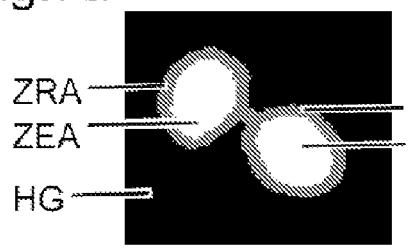
FIG. 7a shows a classification result for a specific image detail from FIG. 3.
Figure 7B:
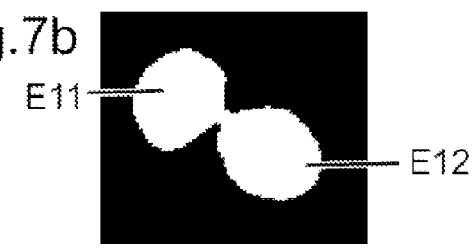
FIG. 7b shows a final classification result of a first type.
Figure 7C:
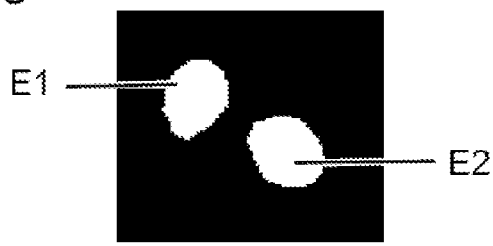
FIG. 7c shows a final classification result of a second type.

FIG. 7a shows for very specific cells ZBA, ZBB from FIG. 6 the classification results from the mapping matrix MX before the mapping step MS1. Pixels which are assigned to the background are depicted in black. Pixels which are assigned to the cell edge are depicted in grey as ZRA. Pixels which are assigned to the cell body or the cell are depicted in white as ZEA. This is also done for the cell ZBB in FIG. 7a by means of the classification of the pixels or image segments and is depicted by means of the information item ZEB and ZRB. Owing to the mapping step MS1, what then advantageously takes place is a separation of the cells ZBA and ZBB, yielding the final information item from FIG. 7c, with the result that these two cells ZBA, ZBB could be separated and could now be ascertained as regions E1, E2. If the mapping is effected incorrectly, for example by the cell edge ZRA, ZRB being assigned to the cell region or cell body ZEA, ZEB, what can occur is that the two cells ZBA, ZBB are interpreted as an entire region, which is depicted in FIG. 7b as a region having the sub-regions E11, E21.

The binary image BSG from FIG. 6 is then processed in a further post-processing step PX from FIG. 11 in order to ascertain the sub-images and to provide them as sub-image data TBD. The step of post-processing PX will now be examined more closely. In order to find relevant contours in the image BSG, post-processing is first carried out by means of the method disclosed in the following reference: Satoshi Suzuki et al., "Topological structural analysis of digitized binary images by border following," Computer Vision, Graphics, and Image Processing, 30(1):32-46, 1985 (incorporated by reference herein in its entirety). Furthermore, so-called bounding boxes are then post-processed by means of the function boundingRect from the section "Structural analysis and shape descriptors" from the database OpenCV (https://opencv.org). Here, the bounding boxes have a size of 150×150 pixels.

Preferably, the fluorescence image SG from FIG. 1 can be assessed in terms of its quality, by at least ten identified cell regions or sub-images having to have a specific morphology and a certain minimum size after ascertainment of the contours in the binary image BSG from FIG. 6. Only when at least ten cells meet both these criteria is there then a further pro-cessing of the fluorescence images without error output in the method. If fewer than ten identified cell regions or sub-images fail to meet the two criteria, the method is preferably aborted and an error message output.

FIGS. 30, 31, 32 and 33 show sub-elements CNNA1, CNNA2, CNNA3, CNNA4, which, considered together in an appropriate sequence, form the convolutional neural network CNNA from FIGS. 10 and 11. According to FIG. 30, the fluorescence image SG is received by the part CNNA1 of the convolutional neural network. As is evident from FIGS. 30 to 33, the entire convolutional neural network CNNA is formed by a sequence of a plurality of steps or processing operation of a neural network, with the occurrence of different types of steps. The first step INL is the so-called input layer, in which the fluorescence image SG of, for example, a 1024×1024 dimensionality is received. The fluorescence image SG from FIG. 1 can preferably have a first dimensionality or resolution which is preferably higher than the resolution 1024×1024 and be scaled down or rescaled to a second dimensionality or resolution of 1024×1024 for the purpose of pre-processing. What preferably takes place in a scaling step SKL is a scaling of the brightness values of the fluorescence image SG to the value range 0 to 1.

Specified in detail for each individual sequential step is the dimensionality of an input variable and the dimensionality of an output variable of a step. In this connection, for each individual step, the dimensionality of the input variable can be found in the top row "Input" between the subsequent brackets through the second and the third entry. Furthermore, what can be found through the fourth entry between the brackets is how many input variables are received in an individual step. A two-dimensional convolution is, for example, carried out in the step CS1, and so the output variable "Output" generates 16 different output variables per input, since 16 convolution kernels are used for the one single input variable, the output variables each having a dimensionality of 512×512. As a result, for each processing step, a person skilled in the art can thus clearly deduce from the parameters specified here the dimensionality of input and output variables and the number of convolution kernels that may have to be used.

Such designs are also found later in the description with regard to the second convolutional neural network CNN2 with reference to FIGS. 23, 24, 25 and 26.

Figure 30A:
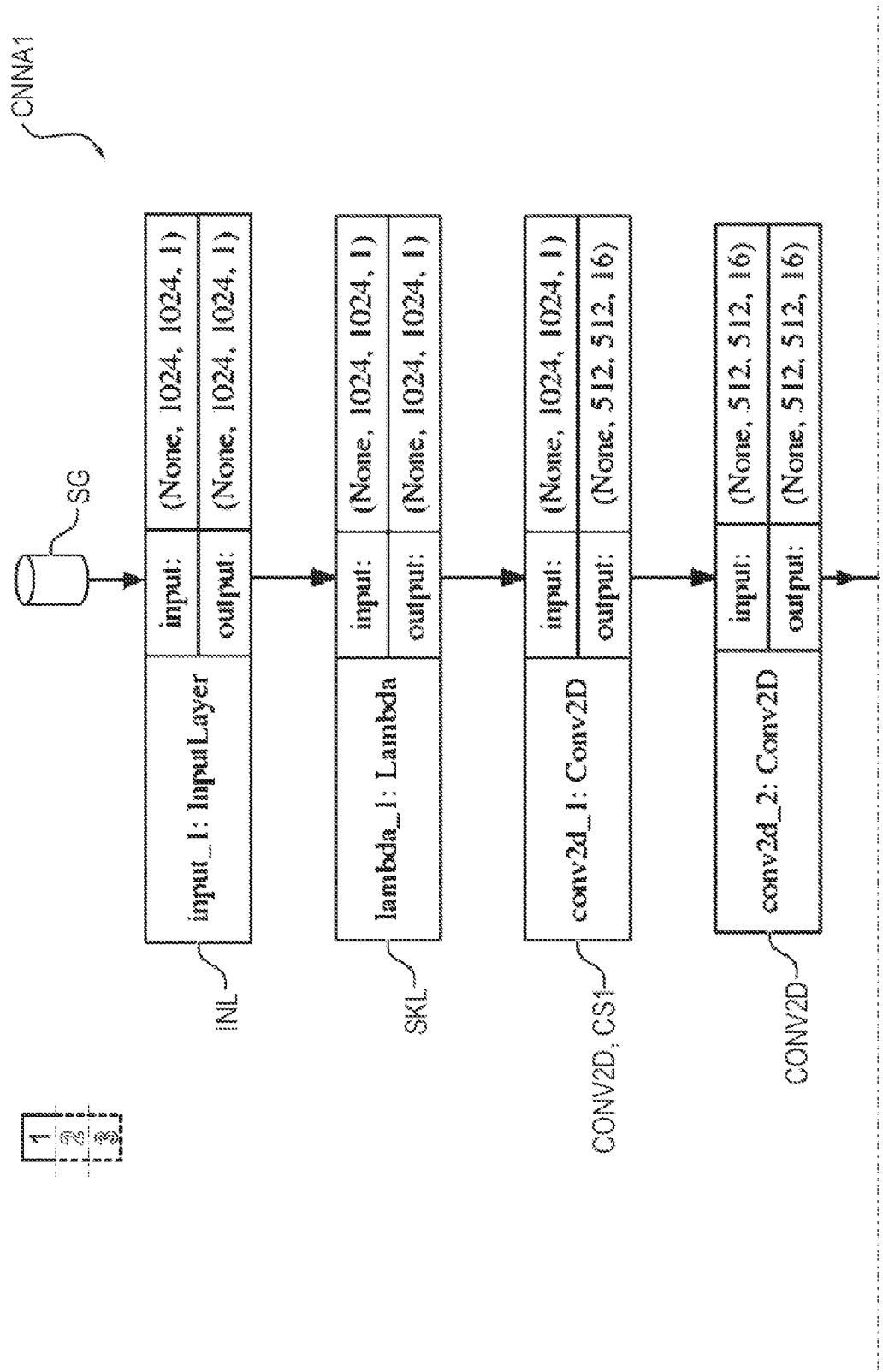
FIGS. 30A to 33B show sub-elements of one embodiment of the second convolutional neural network.
Figure 30B:
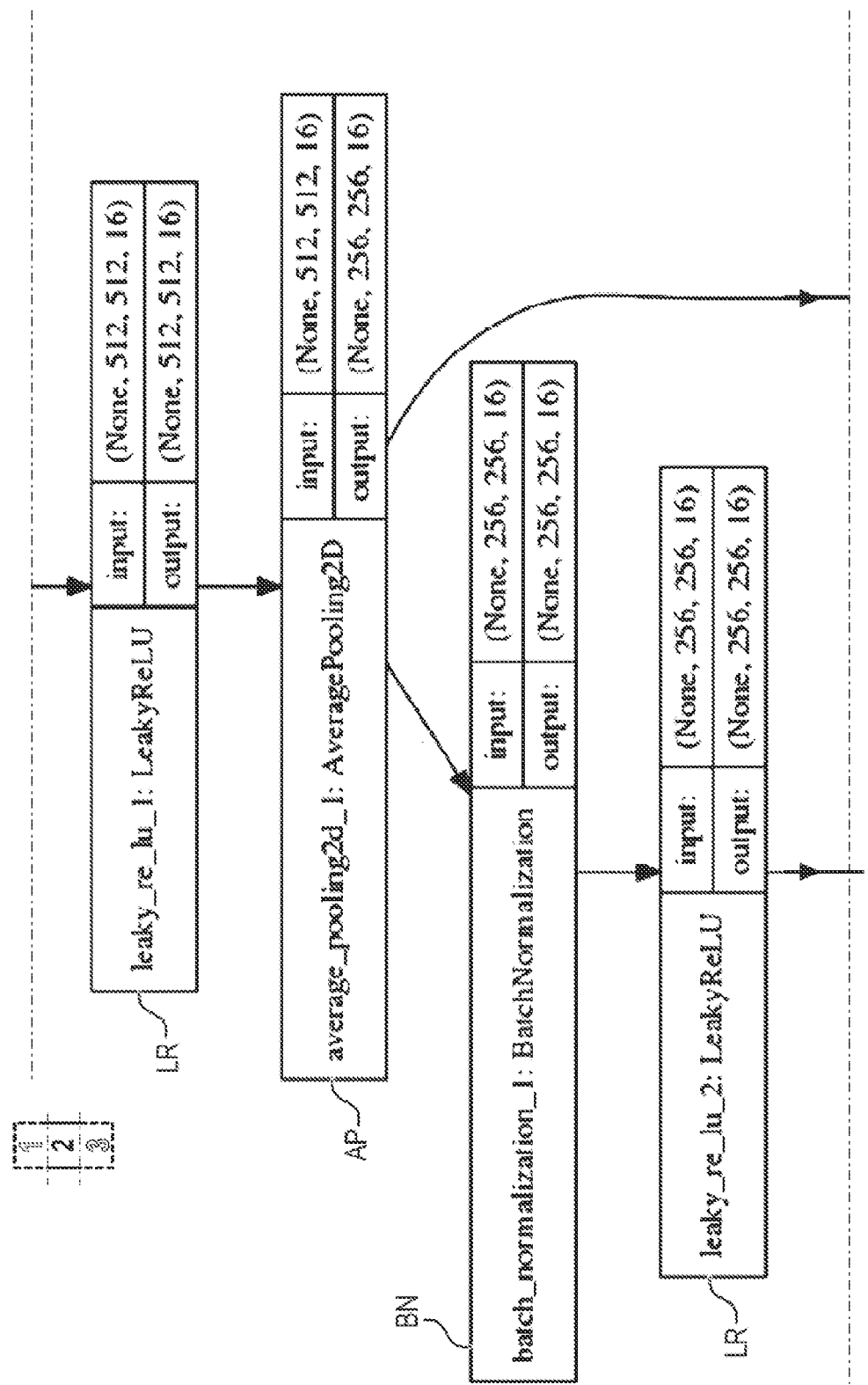
Figure 30C:
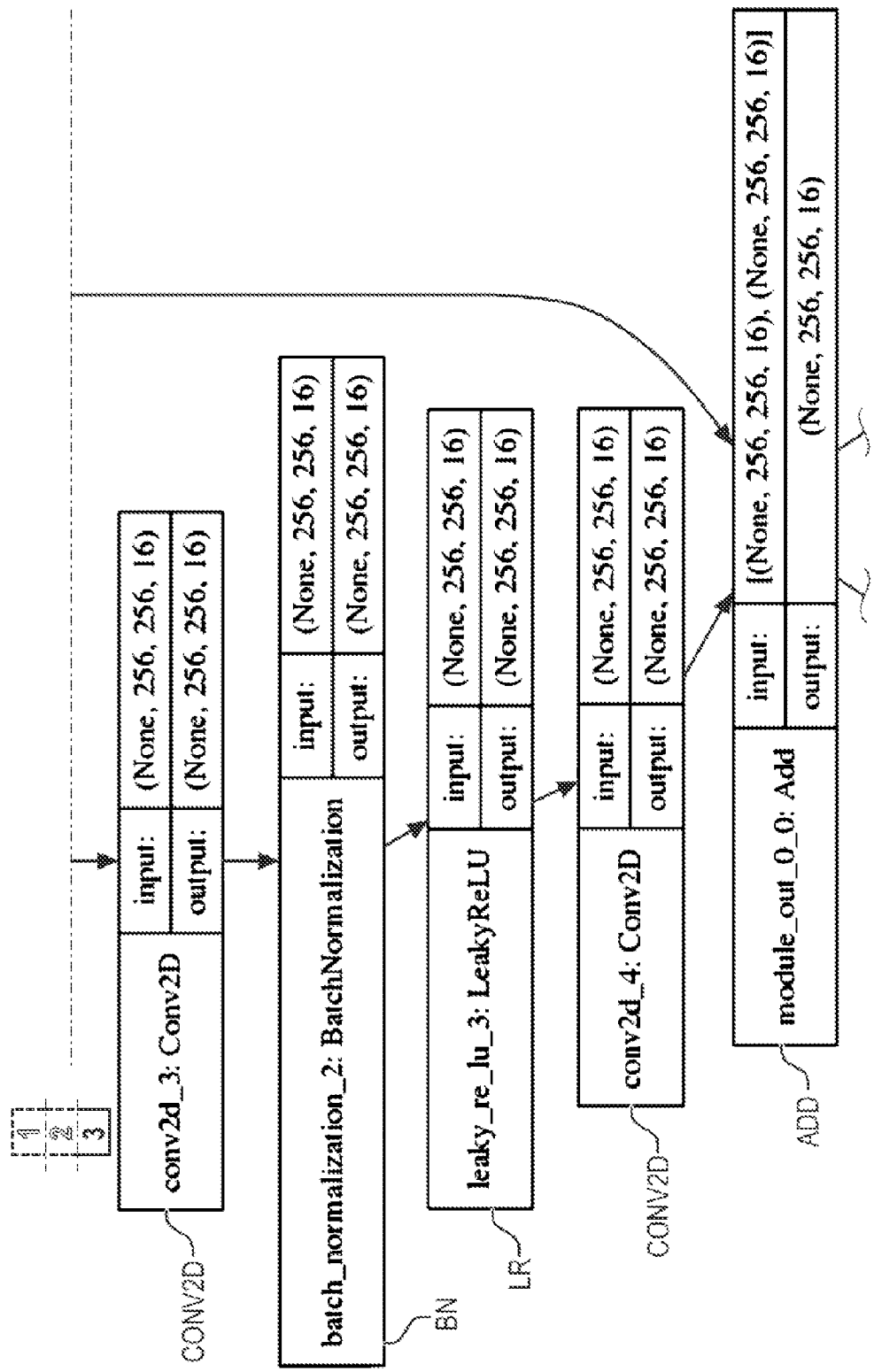
Figure 31A:
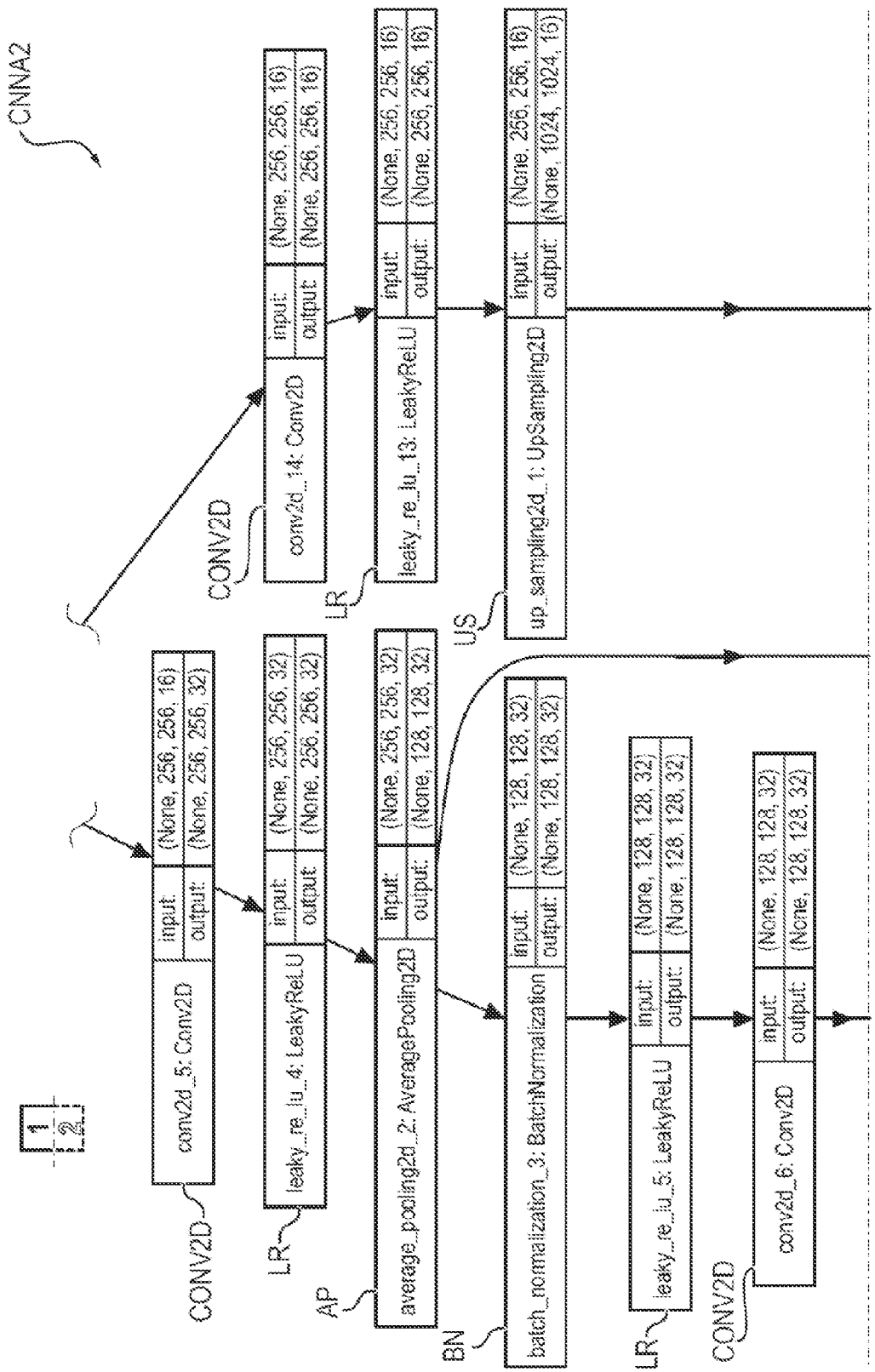
Figure 31B:
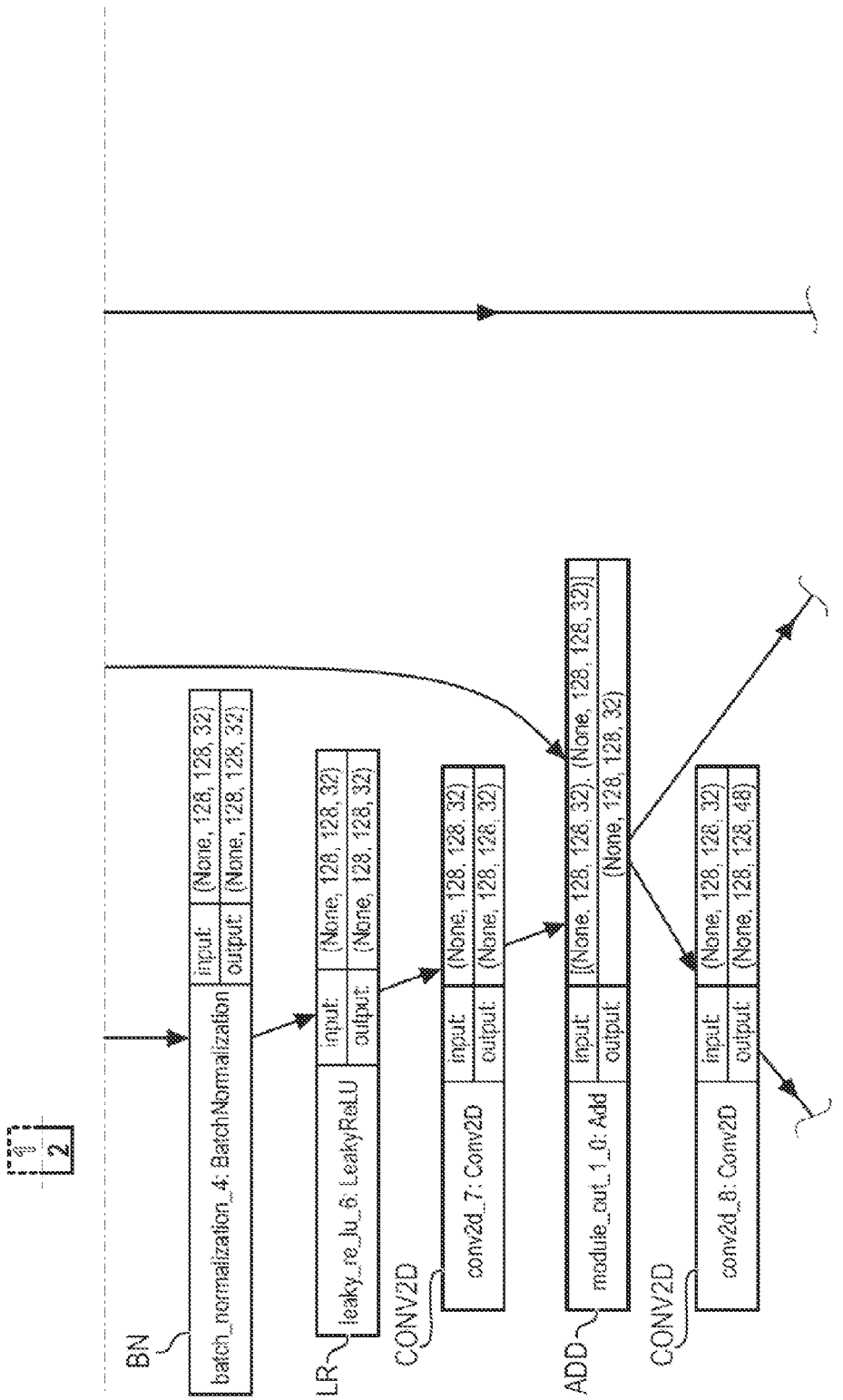
Figure 32A:
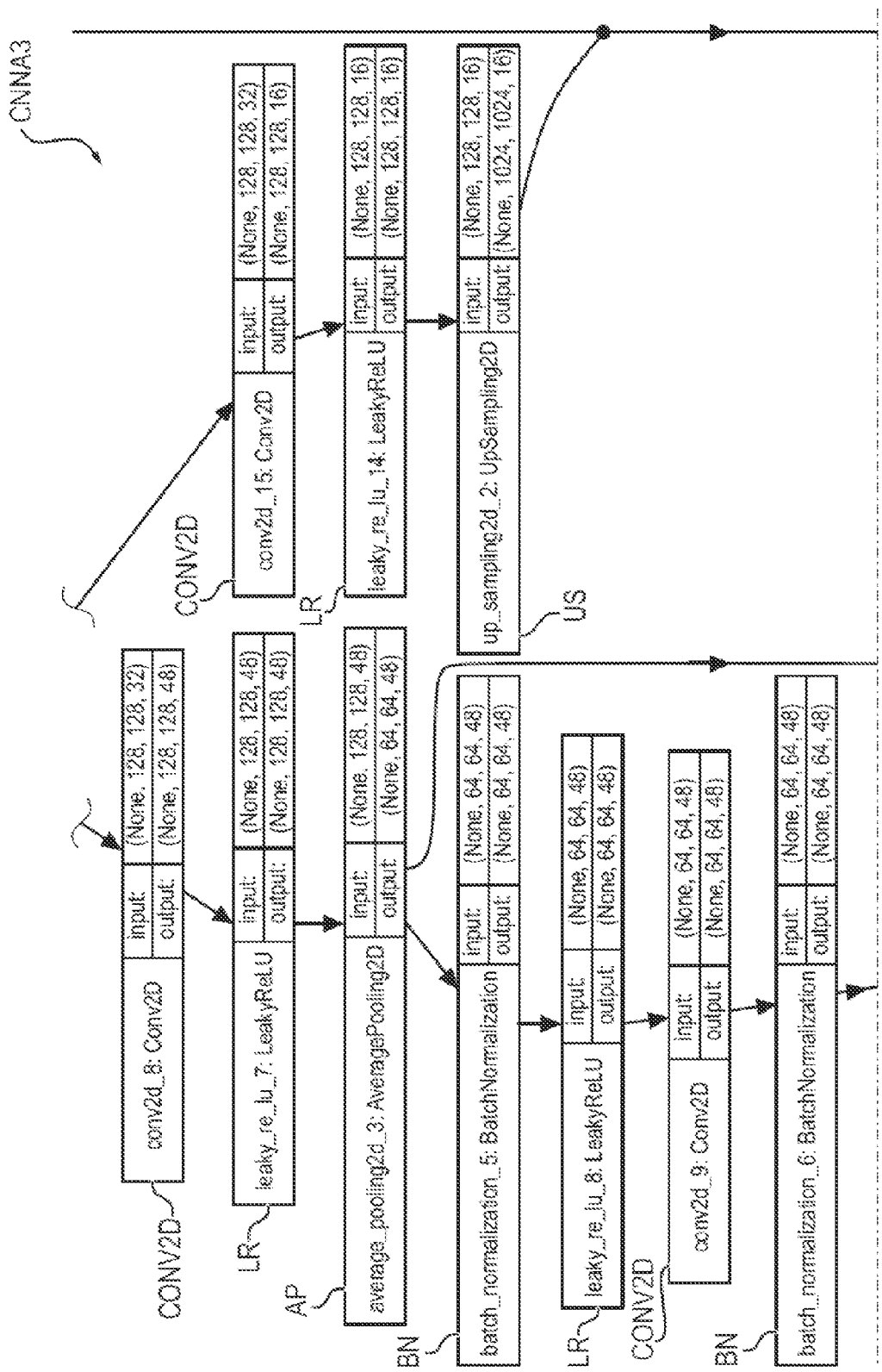
Figure 32B:
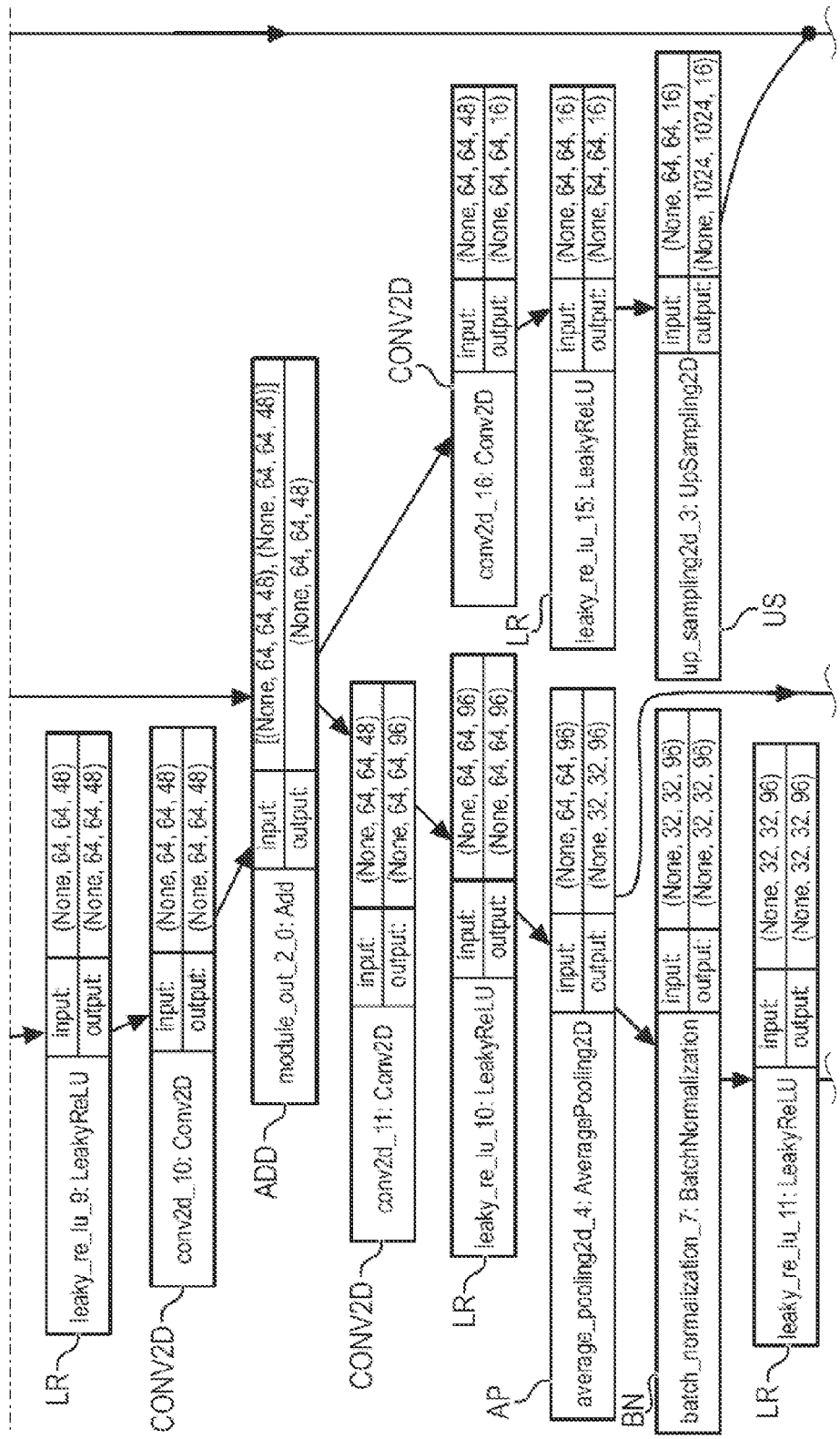
Figure 33A:
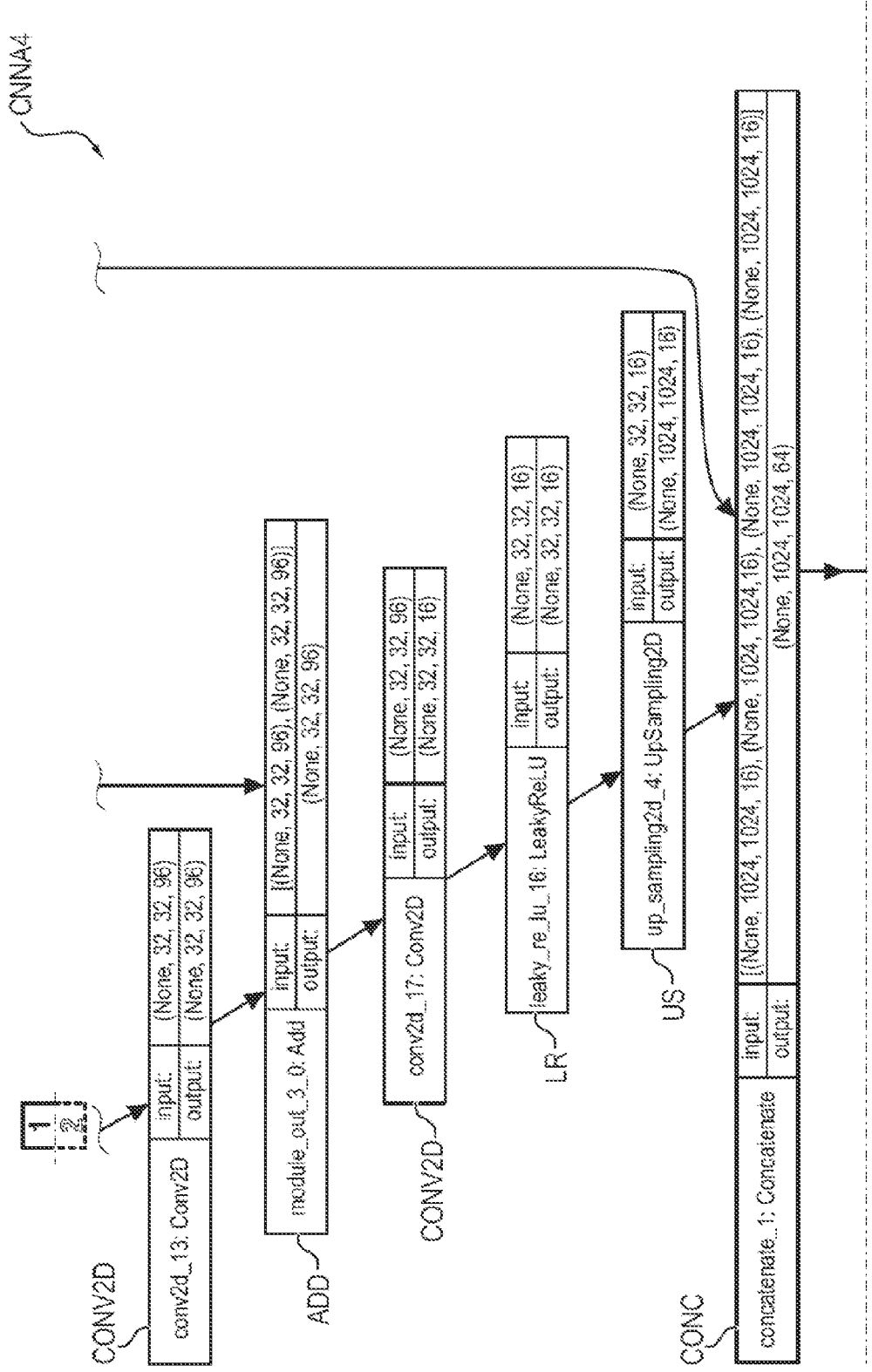
Figure 33B:
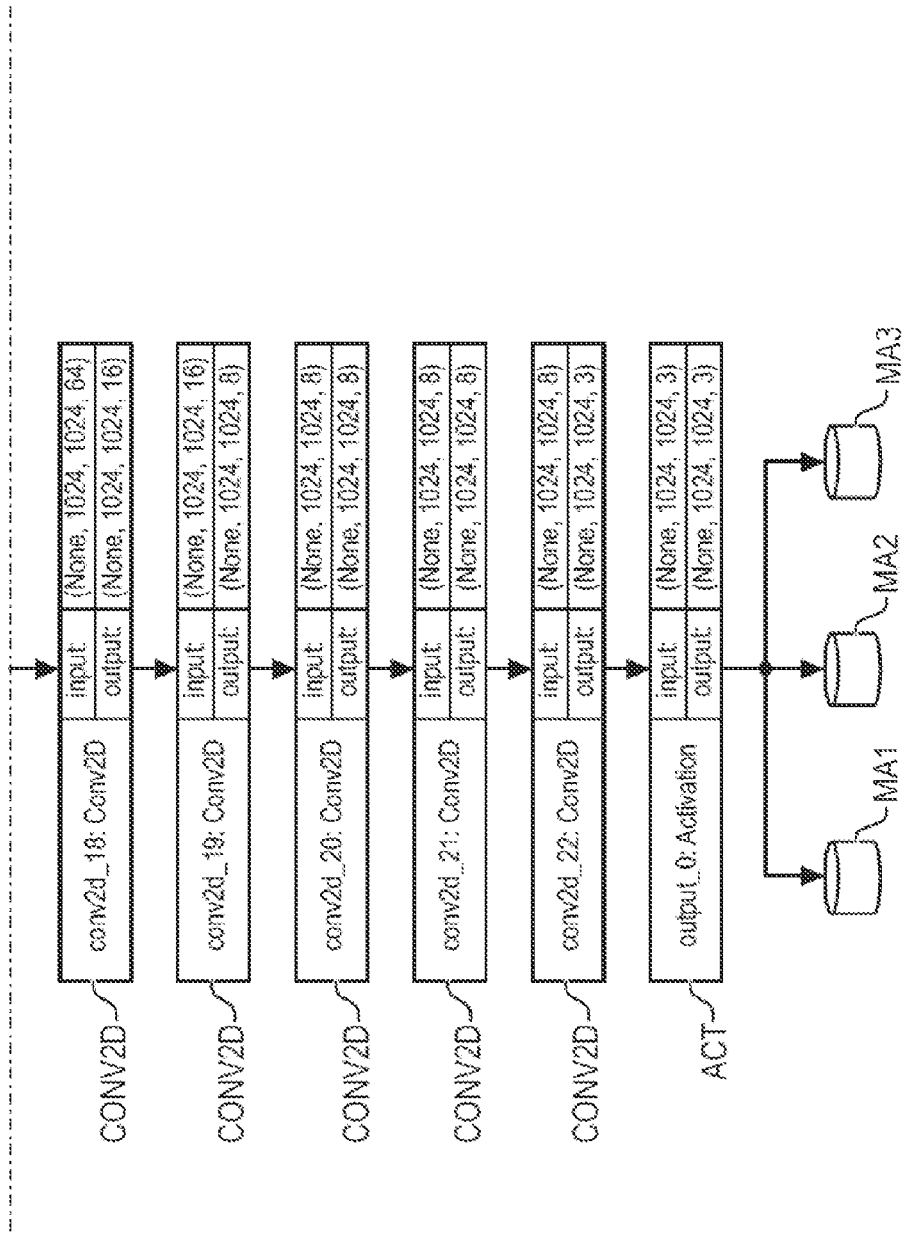

The convolutional neural network CNNA with its components CNNA1 to CNNA4 of FIGS. 30 to 32 comprises different types of processing steps. A processing step CONV2D is a two-dimensional convolution with a specific number of convolution kernels. A function LR is an activation function as a leaky rectified linear unit activation function. A function AP is a so-called average pooling. A function BN is a so-called batch normalization. A processing step or a function ADD is an element-wise addition of multiple input variables for generation of an individual output variable. A processing step US, as depicted in FIG. 31 for example, is a so-called up-sampling. A processing step ACT from FIG. 33 is a so-called activation function which, for example, can be given by a sigmoid function or a so-called softmax function. The output of the neural network CNNA or the output of the sub-network CNNA4 then yields the three matrices MA1, MA2, MA3, which have already been explained in detail with regard to FIG. 11.

Figure 16A:
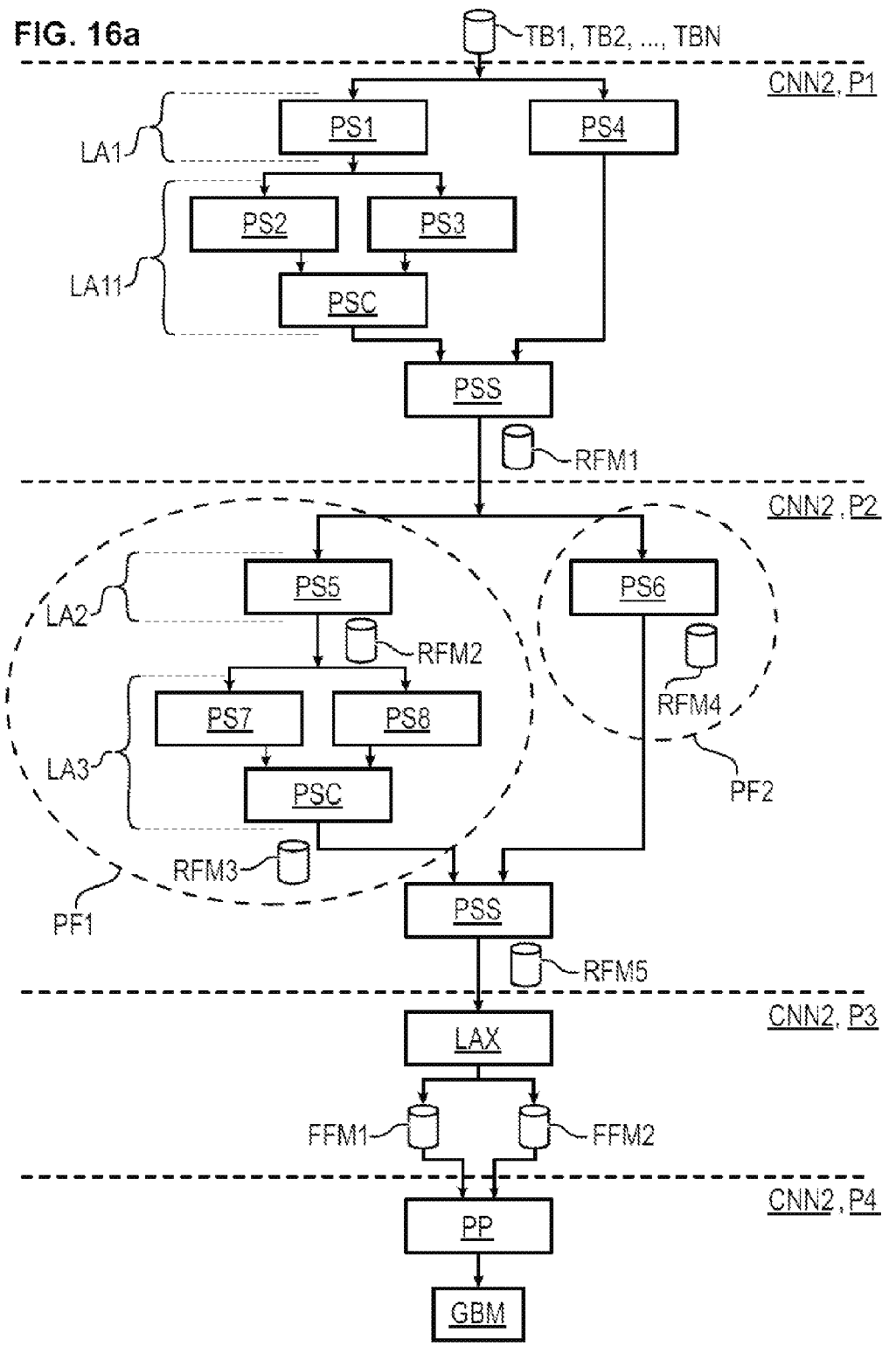
FIG. 16a shows an exemplary illustration of a preferred embodiment of a second convolutional neural network.

FIG. 16a illustrates different processing levels P1, P2, P3, P4 of the second convolutional neural network CNN2 for determining the overall binding measure GBM on the basis of multiple sub-image regions TB1, . . . , TBN as explained above. Here, the CNN2 processes respective sub-image regions TB1, TB2, . . . , TBN with index N separately in order to then generate a respective individual binding measure IBM1, IBM2, . . . , IBMN for a respective sub-image region TB1, TB2, . . . , TBN, as explained above with regard to FIG. 14a.

Here, FIG. 16a shows that, in the course of this determination of the respective individual binding measures for each individual sub-image TB1, . . . , what is then generated is a respective final feature map FFM1 and preferably a further final feature map FFM2. The CNN2 can be configured such that only a single final feature map FFM1 of a single channel is provided and is generated.

The result of the processing level P3 from FIG. 16a is thus a final feature map FFM1 and preferably a further final feature map FFM2 for a sub-image TB with index N. The first final feature map FFM1 is depicted in FIG. 8b for the sub-image TB from FIG. 8a. The second final feature map FFM2 for the sub-image TB is depicted in FIG. 8c.

The convolutional neural network CNN2 solves the problem of a so-called "single-label classification," i.e. whether the kinetoplast in the sub-image exhibits a stain or not. The final feature map FFM1 represents an activation in a first classification channel with regard to a positive decision from the "single-label classification," i.e. that the kinetoplast region is stained. The final feature map FFM2 to be preferably provided represents the corresponding activation with regard to a negative decision, i.e. that the kinetoplast is not significantly stained.

Figure 17:
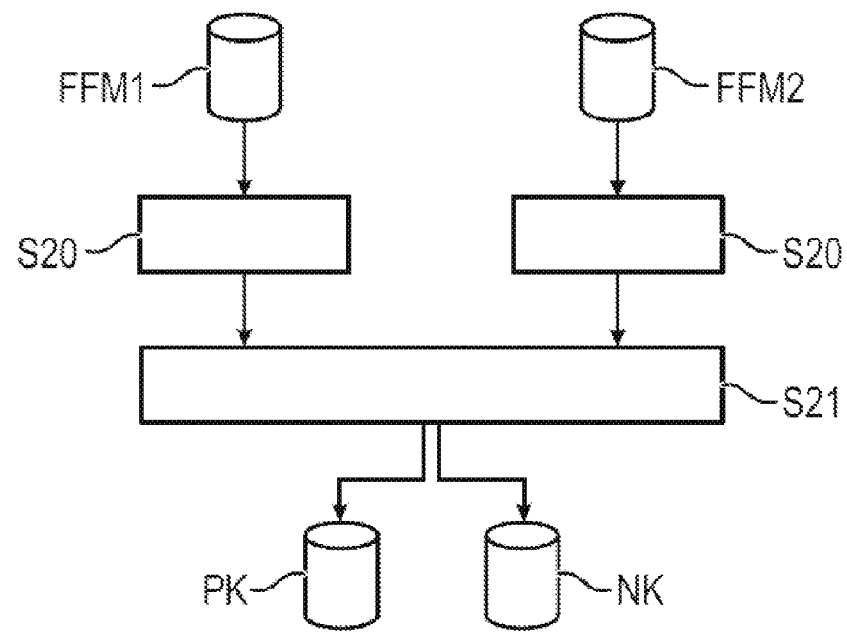
FIG. 17 shows processing steps for determining a confidence measure with regard to a presence of a binding of autoantibodies to a kinetoplast region for a corresponding sub-image on the basis of the associated feature maps.

According to FIG. 17, the first final feature map FFM1 and preferably the second final feature map FFM2 are then used as the basis to determine a positive confidence measure PK with regard to a staining of the kinetoplast region or to a presence of a binding of autoantibodies in the corresponding kinetoplast region K of the contemplated sub-image TB. Preferably, the first final feature map FFM1 and preferably the second final feature map FFM2 are used as the basis to determine a negative confidence measure NK with regard to a staining of the kinetoplast region or to a presence of a binding of autoantibodies in the corresponding kinetoplast region K of the contemplated sub-image TB.

Preferably, only the first final feature map can be used as the basis to determine a confidence measure with regard to a presence of a binding of autoantibodies in a respective kinetoplast region for the respective sub-image TB, without having to use the second final feature map FFM2. It is then, for example, possible in a step S20 to supply the feature map FFM1 to a so-called max pooling, which ascertains for the final feature map FFM1 the maximum pixel value as an individual scalar value. Preferably, said scalar value can be used as the confidence measure. Preferably, said scalar value can then, for example, be used as the basis to ascertain by means of a so-called sigmoid function a value as the confidence measure. Preferably, said scalar value can then, for example, be used as the basis to ascertain by means of a so-called rectified linear unit activation function a value as the confidence measure.

Preferably, in respective steps S20, the two respective feature maps FFM1, FFM2 are each supplied to a so-called max pooling, which in each case ascertains for a respective final feature map the maximum pixel value as a respective individual scalar value. On the basis of said scalar values, it is then possible in a so-called softmax function in a step S21 to determine a positive probability PK as the confidence measure with regard to the presence of the binding of autoantibodies in the kinetoplast region or with regard to a staining of the kinetoplast region. The negative probability NK can likewise be determined by the softmax function. Positive probability PK and negative probability NK preferably form a sum total of value 1 when added. In this way, for a respective sub-image TB, it is thus possible as a result of ascertainment of the first final feature map FFM1 and preferably also the second final feature map FFM2 to then determine according to FIG. 17 a respective confidence measure with regard to the presence of the binding of autoantibodies in the kinetoplast region of the respective sub-image.

Functions which are an alternative to the softmax function are, for example, the sigmoid function, the rectified linear unit activation function or the leaky rectified linear unit activation function.

Figure 18:
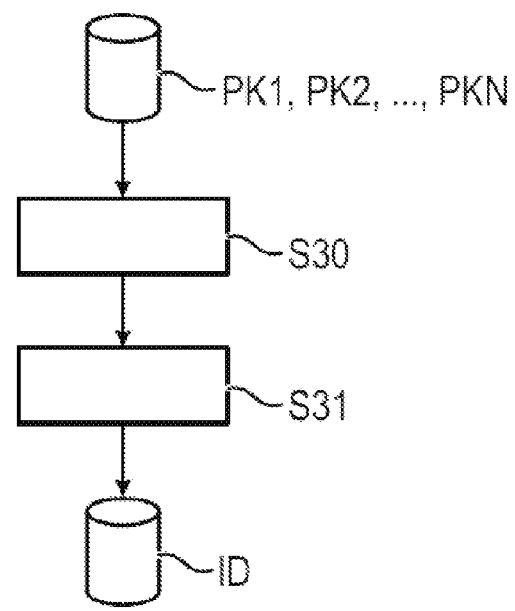
FIG. 18 shows steps for selecting a subset of the identified sub-images on the basis of the confidence measures of the respective sub-images.
Figure 28:
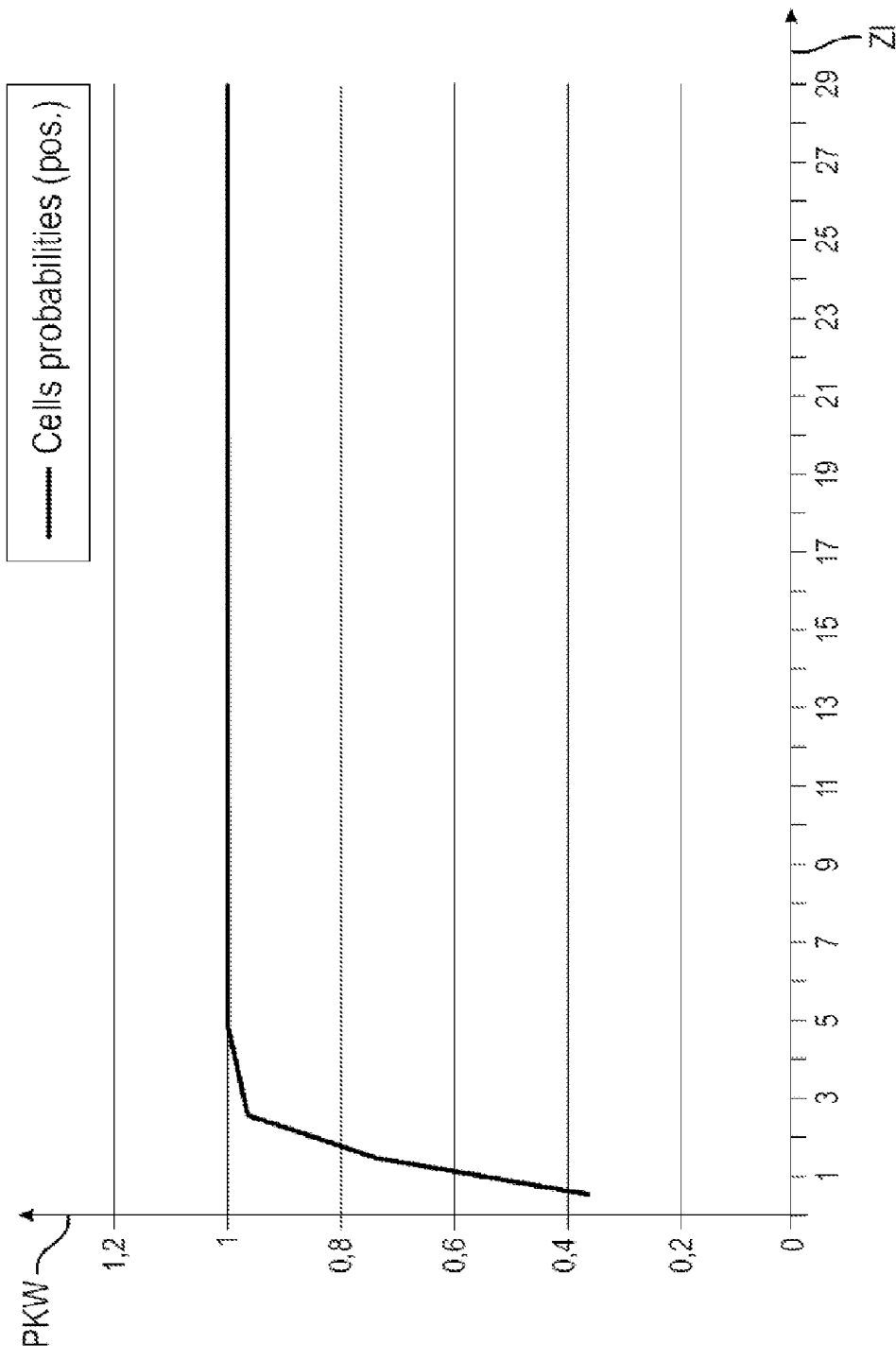
FIG. 28 shows respective confidence measure values for respective sub-images of a fluorescence image.

FIG. 18 shows steps for selecting a subset of the identified sub-images from the fluorescence image on the basis of the respective positive confidence measures of the respective sub-images. The respective positive confidence measures PK1, PK2, PK3, . . . , PKN with index 1, . . . , N of N respective sub-images are sorted in ascending order with respect to their value in a step S30. By way of example, for 29 different Crithidia luciliae cells or for 29 different sub-images, FIG. 28 shows the respectively associated positive confidence measures PK, which are plotted in ascending value with regard to their values PKW via a corresponding sorting index 1, . . . , 29. In the step S31, what are then selected are those confidence measures and their respectively associated sub-images, the associated confidence measure values of which are 50% of the highest confidence measure values PKW. This subordinate set of the associated sub-images is then output or indicated by outputting of the corresponding sub-image indices by means of a data set ID. On the basis of the indices from the data set ID, it is then possible to select the corresponding sub-images and their associated binding measures for a determination of the overall binding measure.

The overall binding measure is then determined on the basis of those binding measures which belong to the selected sub-images. Such an ascertainment of the overall binding measure takes place especially in a step of post-processing PP within the fourth processing level P4 of the second convolutional neural network, as depicted in FIG. 16a.

FIG. 19 shows again an exemplary processing of an individual sub-image TB1 by the second convolutional neural network CNN2. First of all, the sub-image TB1 is processed by the first three processing levels P1 to P3 of the second convolutional neural network, with the result that the final feature map FFM1 and preferably also the second final feature map are provided. In a selection step SEL, what then takes place on the basis of the index data ID elucidated with regard to FIGS. 17 and 18 is the potential selection of the sub-image TB1 into the subset of the sub-images. If the sub-image TB1 has been selected into said subset, what then takes place is further processing as post-processing PP in the fourth processing level P4. Here, after determination of the positive confidence measures and after the selection of the subset of the sub-images, what then takes place is a respective post-processing PI of the respective first feature maps FFM1 of the selected respective sub-images. By way of example, what is thus shown here for an individual sub-image TB1 is a post-processing PI for determining an individual binding measure IBM1. Here, what takes place for the sub-image TB1 is a selection of a respective subordinate image on the basis of the final feature map FFM1. The subordinate image presents a respective kinetoplast region of the corresponding Crithidia luciliae cell in the sub-image. Such a sub-image TB is depicted in FIG. 8a by way of example. The associated first feature map FFM1 from FIG. 8b is then, in a step KIN, adapted in terms of its size and resolution to the sub-image TB from FIG. 8a by means of cubic interpolation, resulting in the enlarged feature map VFM from FIG. 9a.

In a thresholding step SB, a binary-value mask BM, which is depicted in FIG. 9b, is then ascertained. Here, the threshold value preferably used is that value which is half of the maximum possible grey-value intensity of a feature map. Thus, if a grey value of a feature map VFM is between the values 0 and 1, the value 0.5 is used as threshold value.

In a step MS, the masking operator BM from FIG. 9b is then applied to the sub-image TB, yielding the corresponding subordinate image SUB from FIG. 9c. For each respective sub-image TB, the proposed second convolutional neural network CNN2 is thus capable of providing a final feature map FFM1 which indicates by means of its values a subordinate-image region for the sub-image that corresponds to the kinetoplast. The second convolutional neural network is thus capable of cutting out or selecting a corresponding subordinate image from the sub-image that can then be used for the determination of a binding measure of a binding of autoantibodies to double-stranded DNA on the kinetoplasts.

Figure 19:
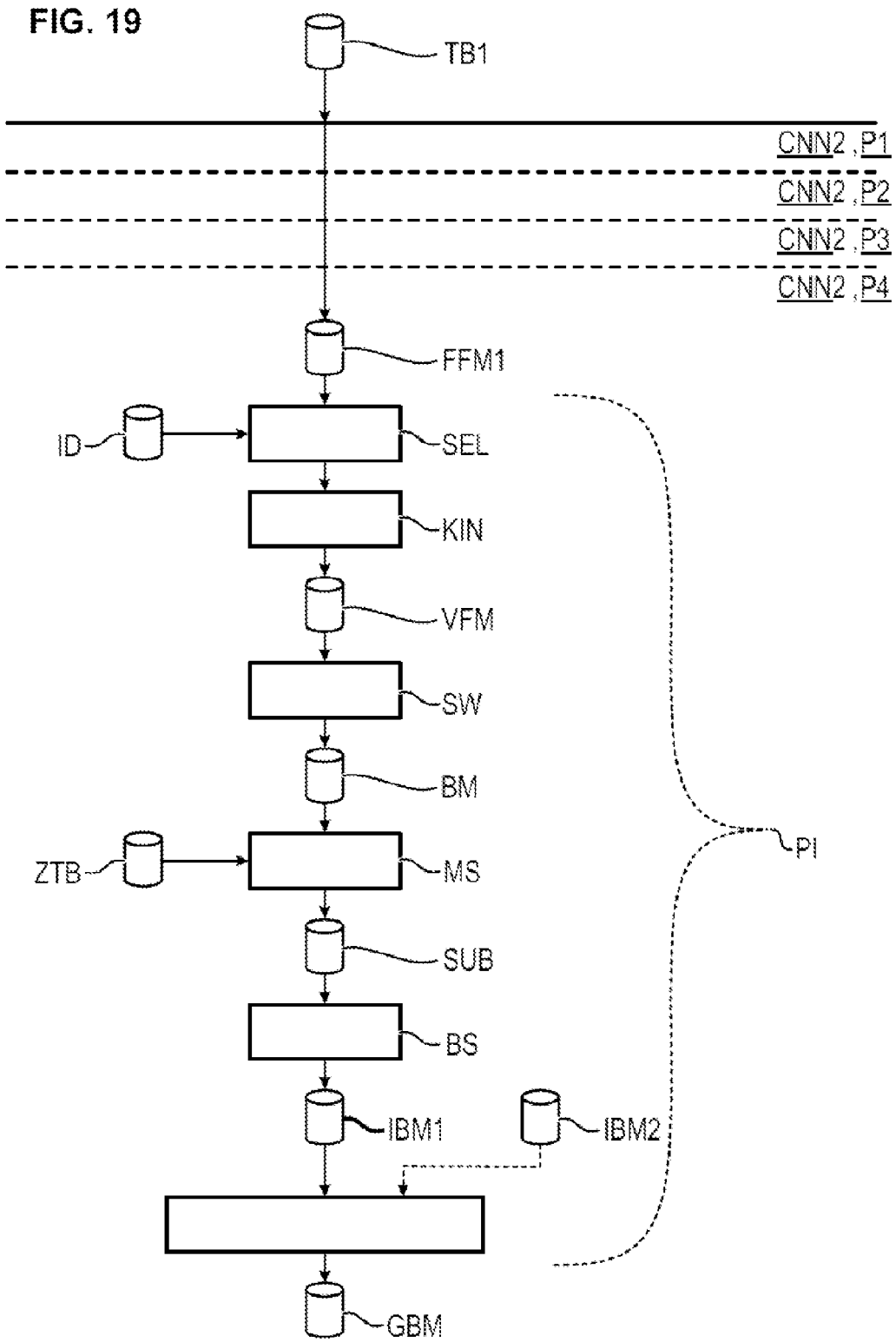
FIG. 19 shows steps for selecting a respective subordinate image of a respective sub-image and for determining a respective binding measure on the basis of the respective subordinate image by means of application of a binary-value masking operator to the respective sub-image.
Figure 27:
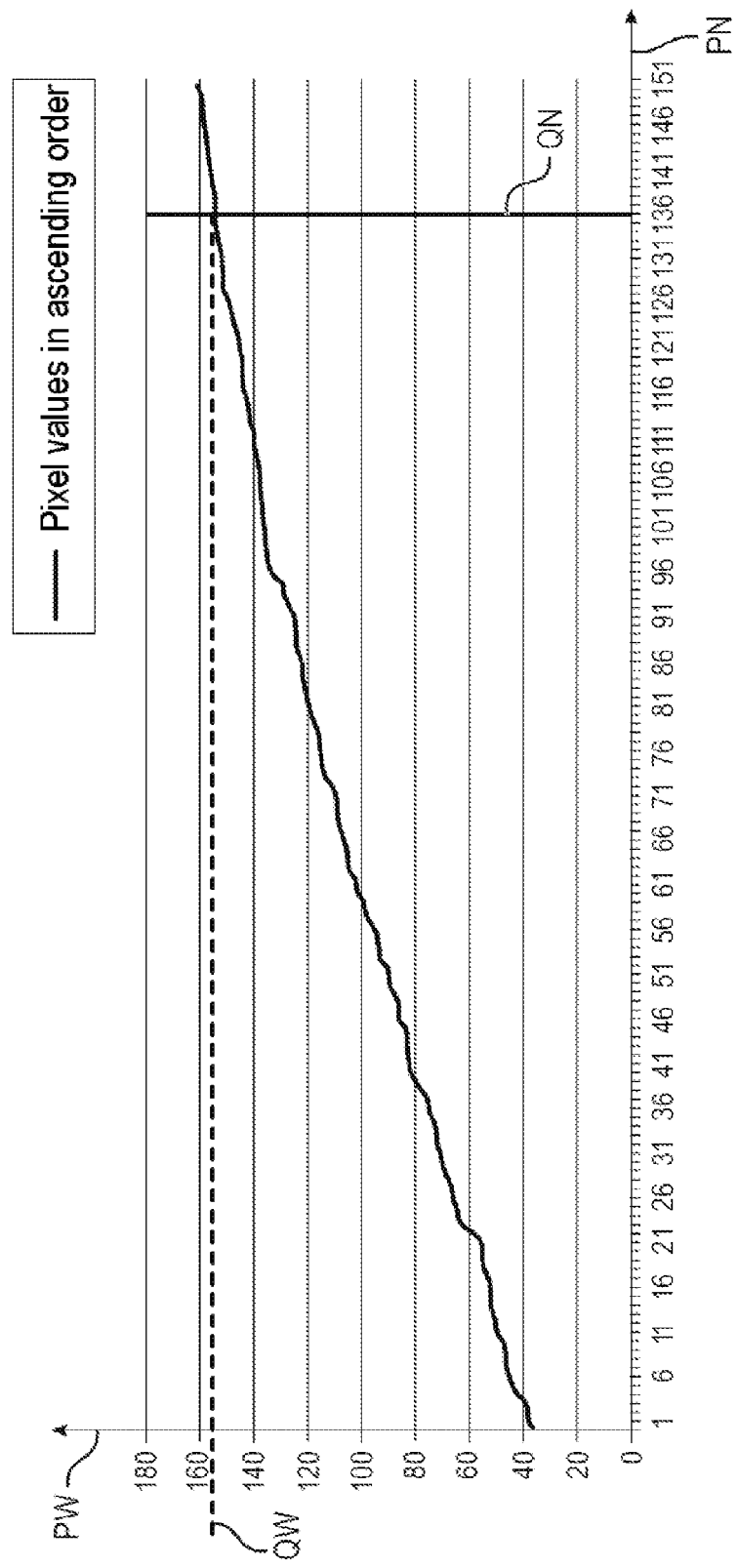
FIG. 27 shows pixel values of a subordinate image.

According to FIG. 19, what is then determined in a determination step BS is the binding measure IBM1 for the sub-image TB1. This is done by looking at the pixel values from the subordinate image SUB and choosing that value which defines the 90% quantile for the pixel values from the subordinate image. In relation to this, FIG. 27 shows, for the pixels of the subordinate image SUB from FIG. 9c, the corresponding pixel values PW in ascending size with corresponding sorting index PN. The value QW for the index QN is that value for which 90% of the pixel values from the subordinate image SUB are smaller than the value QW.

In a following step, the multiple individual binding measures IBM1, IBM2 . . . of the individual sub-images from the selected subset are then used as the basis to determine the overall binding measure GBM.

FIG. 16a shows an exemplary embodiment of the second convolutional neural network CNN2 with multiple processing levels P1, P2, P3, P4 for a respectively separate processing of sub-images TB1, . . . , TBN with index N.

In a first processing level P1, the convolutional neural network CNN2 generates a first set of two-dimensional resultant feature maps RFM1 on the basis of a sub-image TB1 by means of at least one first convolutional layer LA1 and by means of application of multiple two-dimensional convolution kernels. Said feature maps RFM1 need not come directly out of the convolutional layer LA1, but can be generated by means of further processing steps PS2, PS3, PSC.

Figure 16B:
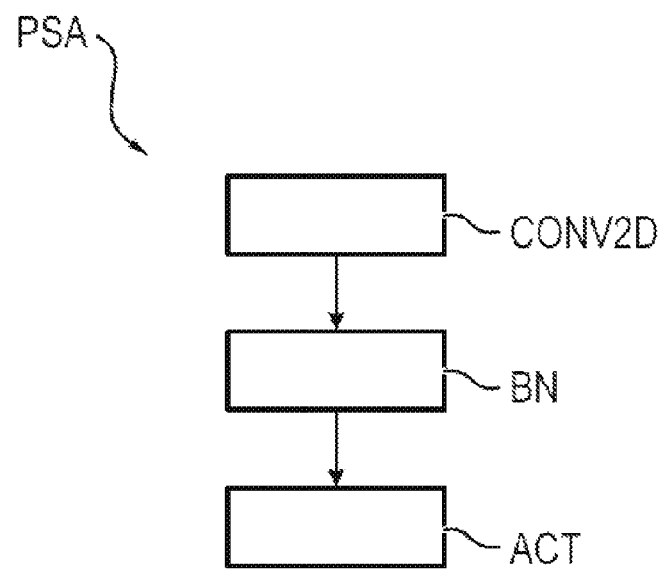
FIG. 16b shows sub-steps of a first type of a convolutional layer of the second convolutional neural network.

In the convolutional layer LA1, what takes place is a processing in a step PS1 with a sequence of different sub-steps. The step PS1 is of the type of a step PSA, which is depicted in detail in FIG. 16b. What takes place first of all is a two-dimensional convolution CONV2D of the incoming sub-image with multiple convolution kernels by means of respective two-dimensional convolutions. A subsequent batch normalization takes place in a step BN. What then follows is a so-called activation in a step ACT.

In the context of this application, a convolutional layer of the second convolutional neural network CNN2 has a layer for convoluting one or more feature maps with one or more convolution kernels. Such a layer for convolution can preferably then be followed within the convolutional layer by a batch normalization layer and/or an activation layer.

In a second processing level P2 from FIG. 16a, what then takes place is a generation of a second set of two-dimensional resultant feature maps RFM2 on the basis of the first set of feature maps RFM1 by means of at least one second convolutional layer LA2 and by means of application of multiple three-dimensional convolution kernels.

On the basis of the second set RFM2, what then takes place is a generation of a third set of two-dimensional resultant feature maps RFM3 by means of at least one third convolutional layer LA3 and by means of application of multiple three-dimensional convolution kernels. Said third set RFM3 enters directly or indirectly into the further processing of the third level P3. In the third level, what takes place is a determination of the first final feature map FFM1 and preferably the second final feature map FFM2 on the basis of the third set RFM3 by means of further convolutional layers LAX.

The second set RFM2 has a smaller number of feature maps than the first set RFM1. Furthermore, the third set RFM3 has a larger number of resultant feature maps than the second set RFM2. A convolution kernel can also be referred to as a convolution operator.

The reduction in the number of feature maps in the second convolutional layer LA2 results in a so-called squeezing. The feature maps of the first set RFM1 or the features thereof are projected into a subspace by means of the convolution kernels, since the three-dimensional convolution kernels respond to feature correlation between the feature maps. Thus, only the most dominant features from the feature maps of the first set RFM1 are retained and projected into feature maps of the second set RFM2. Less dominant and less informative features are thus filtered out as a result.

As a result of the increase in the number of feature maps by the third convolutional layer LA3 from the second set RFM2 towards the third set RFM3, the previously reduced features or information items are distributed among different feature spaces and different feature maps, it being possible to combine the features in different ways owing to the degrees of freedom of the three-dimensional convolution kernels used in the third convolutional layer LA3. This corresponds to a so-called expand.

In the first processing level P1, the first convolutional layer LA1 can be followed by a further convolutional layer LA11. Said layer LA11 uses the feature maps created in the layer LA1. Preferably, the layer LA11 has procession steps PS2, PS3 arranged in parallel to one another. Said procession steps PS2, PS3 are, in each case, of the type of the procession step PSB from FIG. 16c. In a sub-step CONV3D of the step PSB, what takes place is a three-dimensional convolution of the feature maps with respective three-dimensional convolution kernels. What then follows in a further sub-step BN is a so-called batch normalization. What further follows in a step ACT is a so-called activation.

The feature maps resulting from the steps PS2 and PS3 of the layer LA11 are then concatenated with one another in a concatenation step PSC; in other words, the feature maps are joined together.

Preferably, in the first processing level P1, what takes place furthermore is a convolution of the sub-image TB1 in a step PS4 with two-dimensional convolution kernels. The step PS4 is of the type of the sub-step CONV2D from FIG. 16b.

Preferably, the feature maps resulting from the layer LA11 and from the step PS4 can be linked to one another such that the entries of the feature maps are in each case added together in an element-wise manner. Thus, this does not give rise to any change in the dimensionality of the feature maps; instead, the individual elements of the feature maps from the layer LA11 are added in an element-wise manner with the individual elements of the feature maps from the step PS4.

Figure 16C:
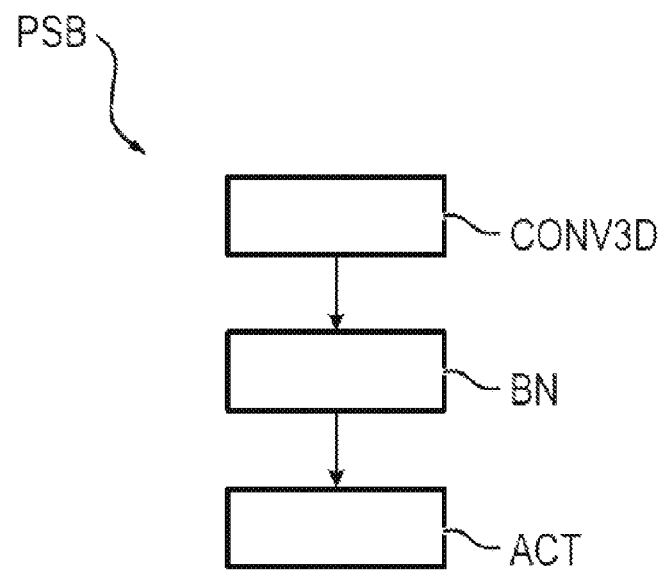
FIG. 16c shows sub-steps of a further type of a convolutional layer of the second convolutional neural network.

The step PS5 from the second convolutional layer LA2 is of the type of step PSB from FIG. 16c.

Preferably, the feature maps from the convolutional layer LA2 are processed in the third convolutional layer LA3 such that, in corresponding steps PS7 and PS8 and in the step PSC, the feature maps are processed in an analogous manner to those from the convolutional layer LA11, it being possible for a number of convolution kernels used and a dimensionality of the convolution kernels to deviate from one another. The steps PS7 and PS8 are of the type of the step PSB from FIG. 16c. As a result of an element-wise addition of the respective feature maps from the respective steps PS7 and PS8, what is then generated by a step PSC is a third set of feature maps RFM3.

In the second processing level P2, the second convolutional layer LA2 and the third convolutional layer LA3 are in a sequence as sub-steps of a sequential processing path PF1. Furthermore, in the second processing level P2, there is in parallel to the sequential processing path PF1 a further processing path PF2 in which the CNN2 generates a fourth set RFM4 of two-dimensional resultant feature maps on the basis of the first set RFM1 by means of at least one fourth convolutional layer LA4 and by means of application of multiple three-dimensional convolution kernels. This is done by a step PS6, which is of the type of the sub-step CONV3D from FIG. 16c.

A set of feature maps RFM5 that is determined by the step PSS in the processing level P2 is then generated in turn from the third set RFM3 of feature maps and the fourth set RFM4 of feature maps by means of a step PSS. Said set of feature maps RFM5 can then be used in a third processing level P3 in order to generate the first final feature map FFM1 and preferably the second final feature map FFM2 by means of further steps LAX, which will be explained in detail later.

In a further processing level PS4, so-called post-processing then takes place, as explained in detail in FIG. 19.

The CNN2 thus generates the final feature map FFM1 corresponding to the sub-image TB on the basis of the third set RFM3 of feature maps and on the basis of the fourth set RFM4 of feature maps. Here, the number of successive convolutional layers LA4 in the parallel processing path PF2 is smaller than the number of successive convolutional layers LA2, LA3 in the sequential processing path PF1. The parallel processing path PF2 thus has fewer convolutional layers than the sequential path PF1. What is made possible as a result in the course of a training of the second convolutional neural network is that, in the event of a recalculation of individual weights of the convolution kernels in the course of a backpropagation, the problem of the so-called vanishing gradient is avoided or reduced.

As stated above with regard to FIG. 16a, the CNN2 can consist of four processing levels.

Figure 23:
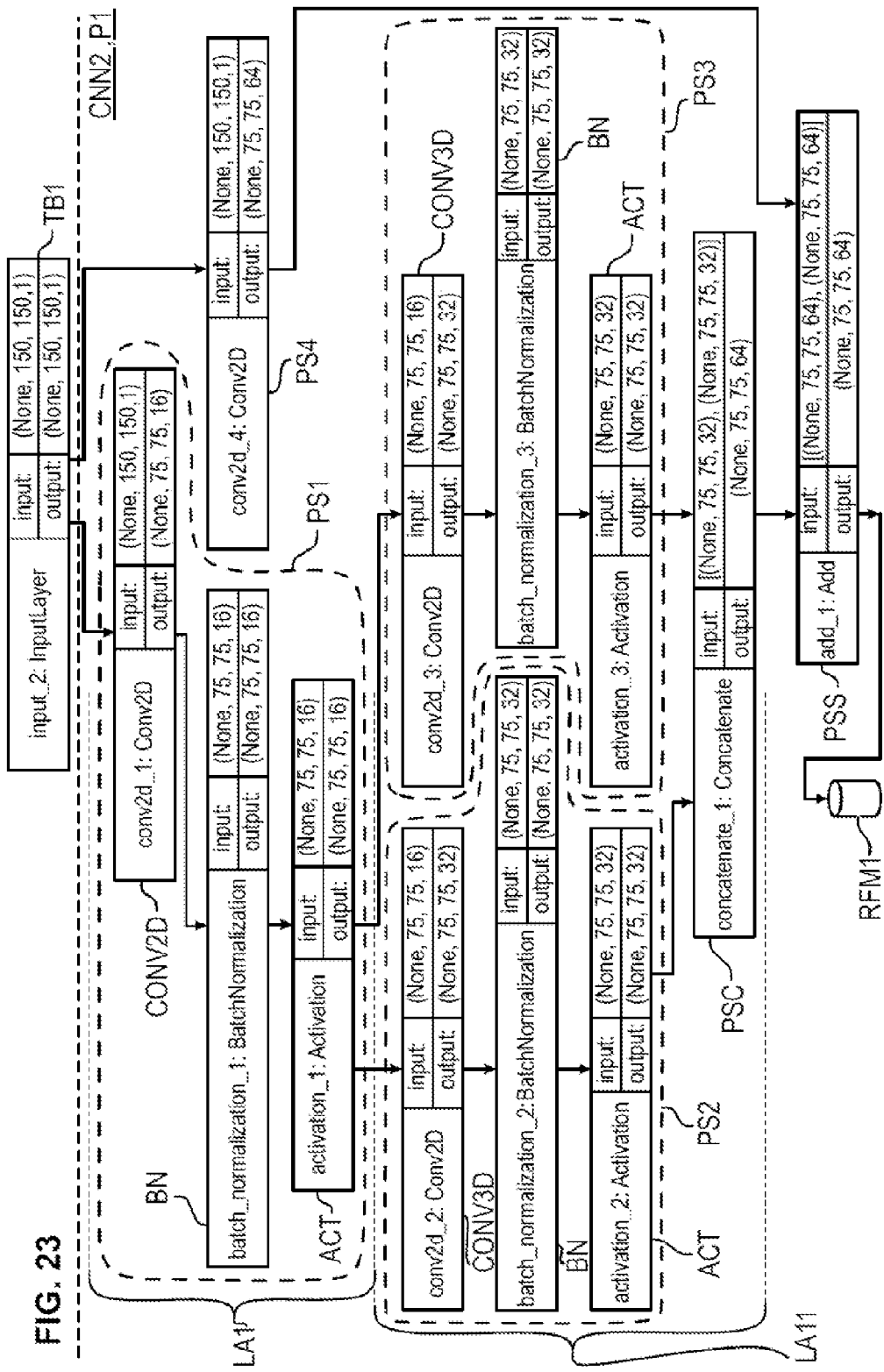
FIG. 23 shows an exemplary embodiment of a first processing level of the CNN2.

In relation to this, FIG. 23 shows a detailed embodiment of the first processing level P1, which corresponds to the first processing level P1 from FIG. 16a.

For each individual step, the dimensionality of an input variable in the form of a sub-image or a set of feature maps is specified in detail. In this connection, for each individual step, the dimensionality of the input variable(s) can be found in the top row "Input" between subsequent brackets through the second and third entry. For example, the sub-image data TB1 are of a dimensionality of 150×150 pixels. For the data TB1, there is only a single input variable, which is indicated by the element "1" in the fourth/last entry between the brackets. In terms of their value range, the image data TB1 are preferably normalized to a value range of from 0 to 1.

In the step PS, said input variable TB1 is, for example, then processed with a convolution kernel such that feature maps of a dimensionality of 75×75 pixels result. In this connection, the last entry in the bottom row "Output" indicates the number of generated feature maps in the resultant set of feature maps. As a result, for each processing step, a person skilled in the art can thus clearly deduce from the parameters specified here, how many convolution kernels must be applied to incoming data TB1 or incoming feature maps in order to arrive at a specific number of outgoing feature maps. In the example of the step PS4, these are 64 convolution kernels. Furthermore, a person skilled in the art can deduce on the basis of the specified dimensionality of the incoming feature maps and the specified dimensionality of the outgoing feature maps, how far a so-called striding, i.e. a shift during the convolution of a feature map with a convolution kernel, must be performed by a specific number of pixels. In the example of the step PS4, this is a striding of the value 2.

A person skilled in the art is given clear instructions for configuring the processing level P1 of the convolutional neural network CNN2 by the information specified in FIG. 23.

Figure 24:
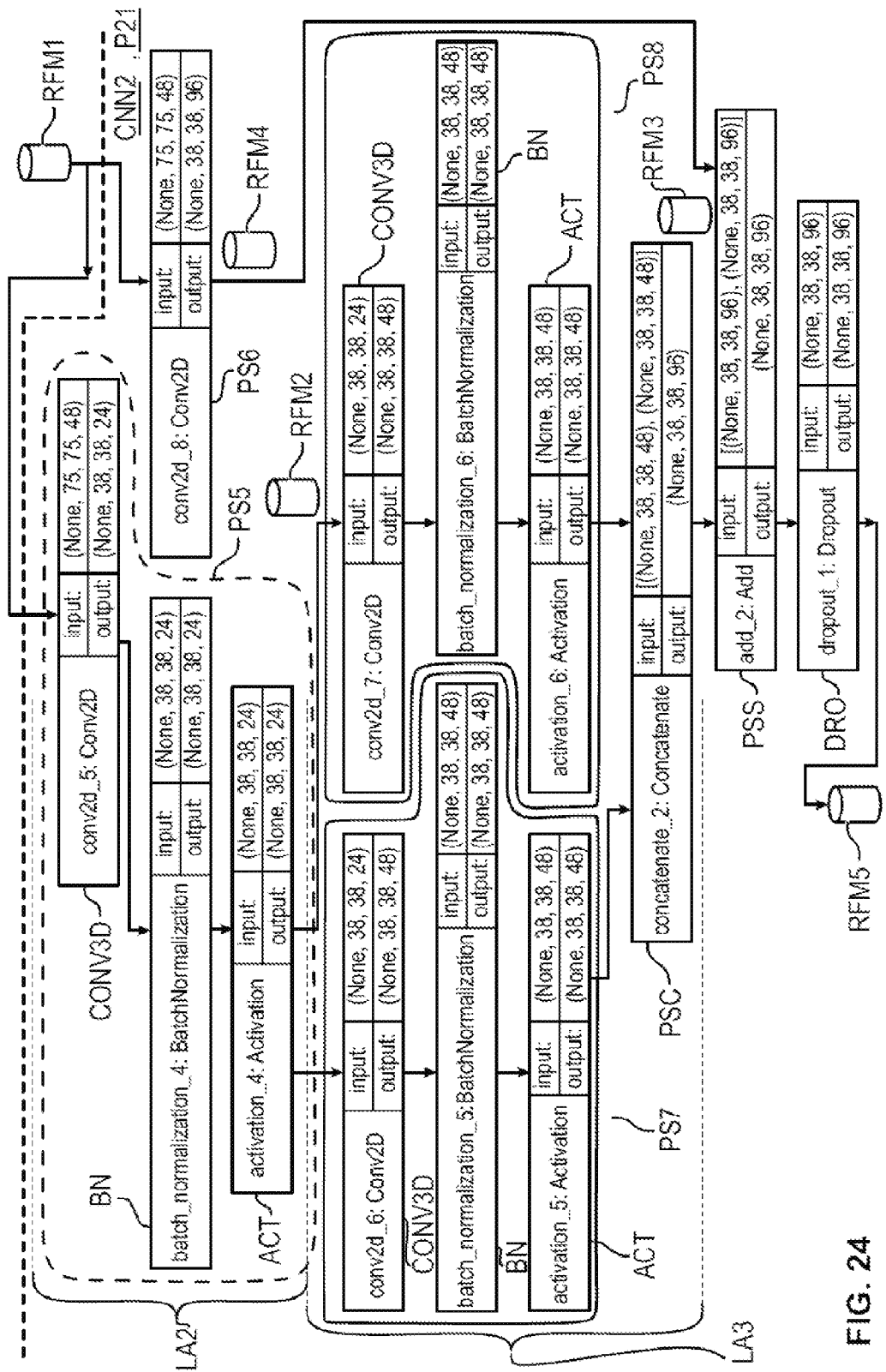
FIG. 24 shows an exemplary embodiment of a first part of a second processing level of the CNN2.

FIG. 24 shows a first part P21 of the processing level P2 from FIG. 16a. Here, the structure of the sub-processing level P21 substantially corresponds to the processing level P2 from FIG. 16a. In addition, there is further provided here a so-called dropout step for the training phase, in which individual entries of the feature maps are set to the value "0" (zero) in terms of their pixel values during the training, but not during the actual classification in the test phase. Here, the drop factor is preferably a value of 50%, meaning that half of the pixel values are set to zero. The pixel values are randomly chosen, by selection of their indices by means of a random function.

What then results in the sub-processing level P21 is the set RFM5 of feature maps, as shown above in the processing level P2 in FIG. 16a.

Preferably, the convolutional neural network CNN2 can have a further sub-processing level P22, which was not depicted above in FIG. 16a. Here, the set of feature maps RFM5 is further processed in order to generate a modified set of feature maps RFM51.

Figure 25:
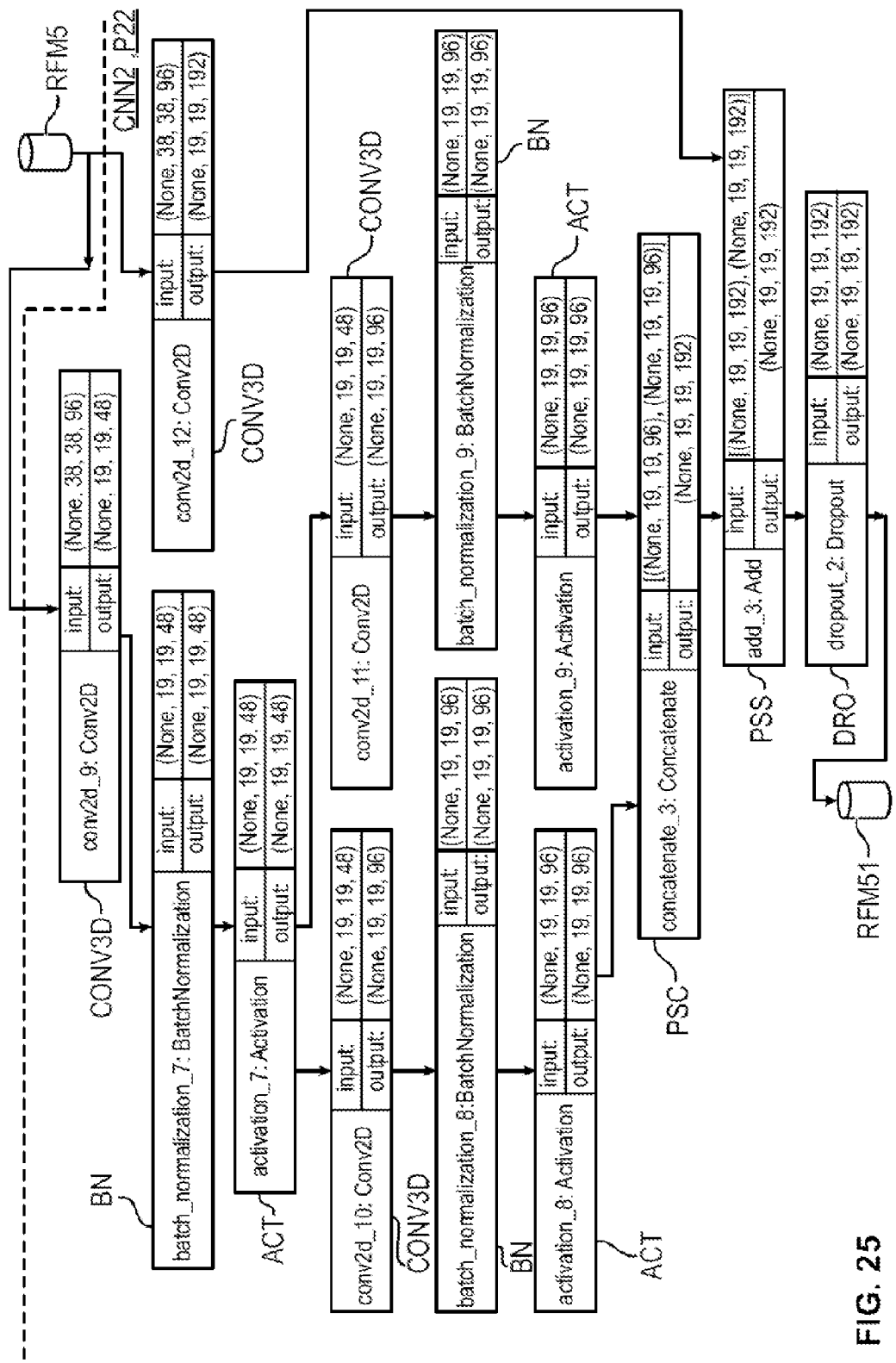
FIG. 25 shows an exemplary embodiment of a second part of a second processing level of the CNN2.

Here too, FIG. 25 contains precise information for a person skilled in the art as to how said modified set of feature maps RFM51 is to be generated. Here too, a so-called dropout DRO takes place during the training phase, but not the test phase.

Figure 26:
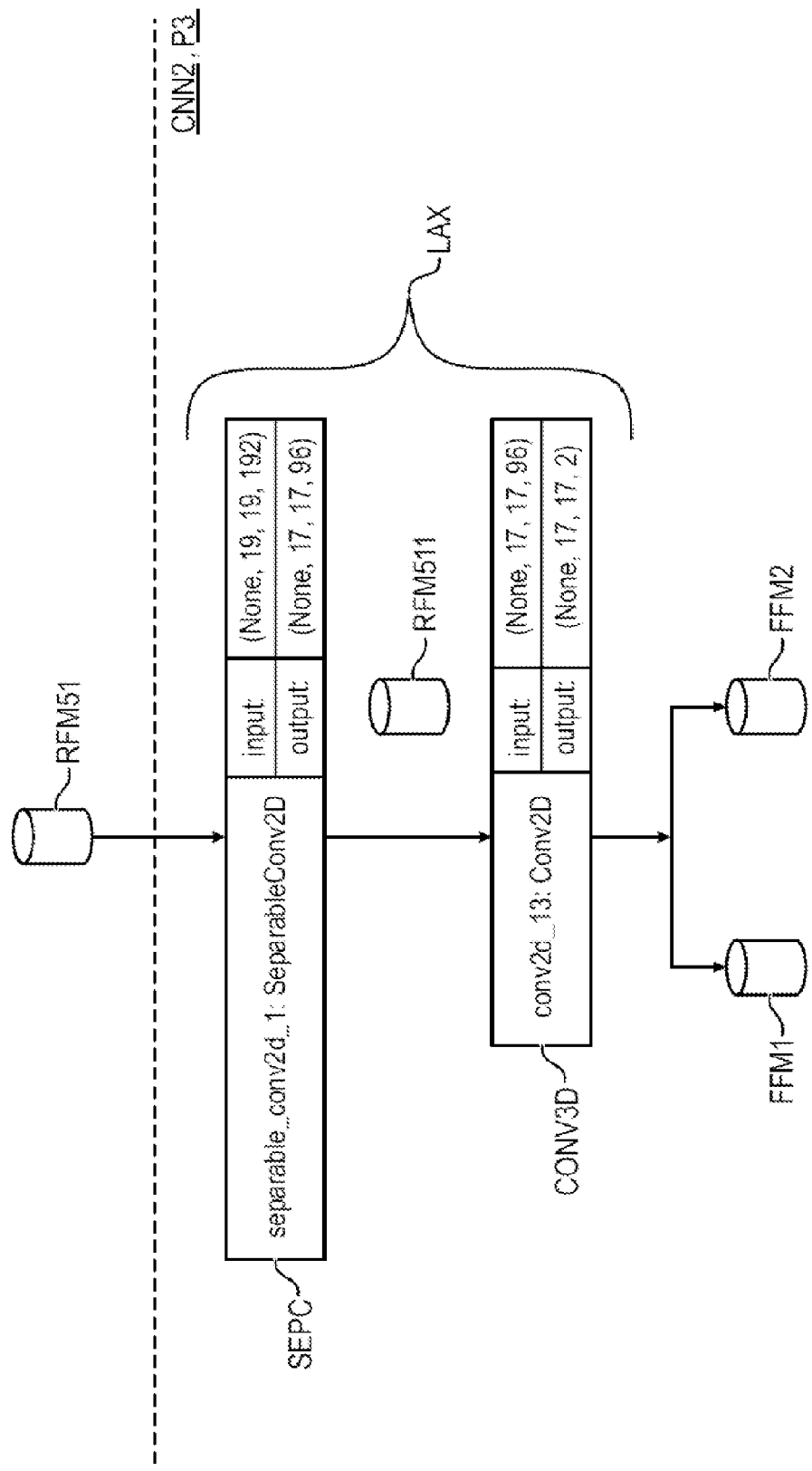
FIG. 26 shows an exemplary embodiment of a third processing level of the CNN2.

FIG. 26 shows one embodiment of the third processing level P3 for generating the first final feature map FFM1 and preferably the second final feature map FFM2. The feature map FFM1 and preferably the feature map FFM2 are generated indirectly on the basis of the third set of feature maps RFM3 and the fourth set RFM4 of feature maps. Here, the processing step LAX, which was depicted above in FIG. 16a, has sub-steps. In a first sub step SEPC, what takes place is a so-called "depth-wise convolution" of the incoming feature maps RFM51, in which each individual two-dimensional feature map from the set RFM51 is separately convoluted with a two-dimensional convolution kernel, yielding a set of two-dimensional feature maps RFM511. What then takes place immediately afterwards in a further sub-step CONV3D is a convolution of the multiple two-dimensional feature maps of the set RFM511 that result from the step SEPC with a three-dimensional convolution kernel of the dimensionality 1×1×G, where G is the number of feature maps in the set, with the result that the first final feature map FFM1 is determined therefrom. Preferably, what also takes place furthermore in the further sub-step CONV3D is a further convolution of the multiple two-dimensional feature maps of the set RFM511 that result from the step SEPC with a further three-dimensional convolution kernel of the dimensionality 1×1×G, where G is the number of feature maps in the set, with the result that the second final feature map FFM2 is determined therefrom.

The third processing level P3 from FIG. 26 is then followed by so-called post-processing PP, as indicated in the processing level P4 in FIG. 16a and as explained in detail in FIG. 19.

For an implementation of one or more exemplary embodiments of the convolutional neural networks CNN1, CNN2 proposed here, a person skilled in the art can have recourse to a so-called open-source deep-learning library called "Keras." Detailed information is found under https://keras.io by a person skilled in the art. The embodiment of the proposed CNN2 with the processing levels P1, P21, P22 and P3 from FIGS. 23 to 26 and also the processing level P4, as illustrated in detail in FIG. 19, was created for test purposes by means of the so-called open-source deep-learning library "Keras."

Various data sets of fluorescence images were used for a training of the convolutional neural networks CNN1, CNN2.

The training of the first convolutional neural network CNN1 was based on 34 000 entire images or fluorescence images with corresponding ground-truth data of the three image segment classes cell body, cell edge and background. For the training, 95% of the 34 000 fluorescence images were used, i.e. 32 300 fluorescence images. During the training, these 32 300 were supplied to the first convolutional neural network and optimized by means of cross-entropy loss to reproduce the ground-truth masks. The training was carried out with a start learning rate of 1e-3 for 100 epochs. The learning rate was variable and dependent on the current epoch. For a subsequent test of the first convolutional neural network CNN1, the remaining 5% of the 34 000 fluorescence images were then used, i.e. 1700 fluorescence images. Corresponding ground-truth data of the three image segment classes cell body, cell edge and background were also present. The classification of the image segments was done at the pixel level or with pixel accuracy. What was achieved was a 99.6% accuracy of the classification of the image segments or pixels based on the 3 classes. A further metric evaluated was the mean intersection over union (Miou), because it considers the strong imbalance between the frequency of background pixels and cell pixels. A Miou of 80% was achieved.

The first data set of fluorescence images was one in which it was known that the patient samples used for incubation have autoantibodies and that the kinetoplast regions thus have a relevant staining in the fluorescence images. The second data set of fluorescence images was one in which it was known that the patient samples used for incubation have no antibodies and that the kinetoplast regions thus have no relevant staining in the fluorescence images.

The training of the second convolutional neural network CNN2 was based on 24 980 sub-images which represented the "positive" test case (positive finding or positive patient) and on 15 957 sub-images which represented the "negative" test case (negative finding or negative patient). For the training itself, use was then made of 17 427 positive sub-images from the entire 24 980 positive sub-images and of 11 233 negative sub-images from the entire 15 957 negative sub-images, with corresponding ground-truth information in each case. The second convolutional neural network CNN2 was trained in 100 epochs using a learning rate of 1e-3. For the testing, use was then made of 7543 positive sub-images from the entire 24 980 positive sub-images and of 4724 negative sub-images from the entire 15 957 negative sub-images. The decisions arrived at by the second convolutional neural network CNN2 in the test case then yielded 6602 true positive decisions and 4623 true negative decisions. Further yielded was 101 false positive decisions and 941 false negative decisions. This corresponds to a sensitivity of 87.52% and a specificity of 97.86%.

Figure 29:
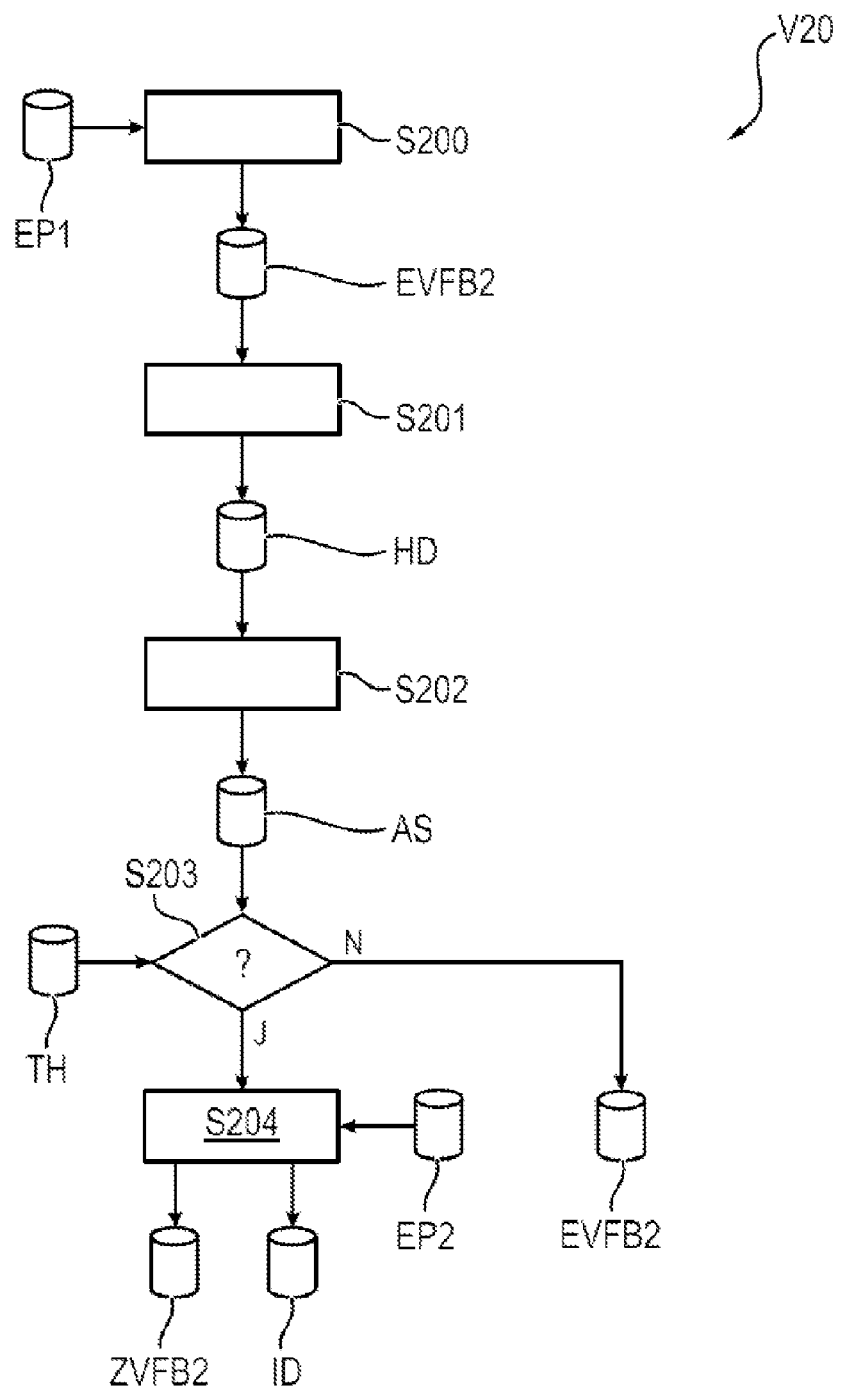
FIG. 29 shows steps of a method for acquiring a fluorescence image according to a preferred embodiment.

FIG. 29 shows a method V20, in which preferably performable steps for acquiring the fluorescence image are carried out.

In a step S200, a first preliminary fluorescence image EVFB2 is acquired by means of at least one predefined acquisition parameter EP1, which is preferably a gain parameter.

In a step S201, a histogram is then formed across the pixel values of the image EVFB2, so that the histogram data HD are ascertained and provided.

In a step S202, the number of pixels exceeding a specific saturation with respect to a brightness is then established. For an exemplary quantization range of the pixel values of from 0 to 255, what is established for example is how many pixels have a pixel value or a grey value of 255. This number of pixels which are in brightness saturation are provided as data AS.

In a step S203, a check is then made as to whether the number of pixels AS which are within a saturation range exceeds a predefined threshold value TH. If there is no exceeding of the threshold value (see branch "N"), the first preliminary fluorescence image EVFB2 is used as the fluorescence image SG; see FIG. 4. If the number of pixels which are in saturation exceeds the threshold value TH (see branch "Y"), a second preliminary fluorescence image ZVFB2 is acquired in a step S204 using at least one second predefined acquisition parameter EP2. The predefined acquisition parameter EP2 differs from the previously predefined first acquisition parameter EP1. Preferably, the acquisition parameter EP2 is a gain parameter and is smaller than the first acquisition parameter EP1, meaning that the image ZVFB2 is lit less strongly than the image EVFB2. The acquired second preliminary fluorescence image EVFB2 is then used as the fluorescence image SG; see FIG. 4. Preferably, what are furthermore provided are indicator data which indicate that the brightness of the first preliminary fluorescence image EVFB2 has exceeded a maximum brightness and that the fluorescence image SG is a second preliminary fluorescence image ZVFB2 that has been acquired with reduced brightness.

The second preliminary fluorescence image EVFB2 can then be used in the usual way in the proposed method as the fluorescence image SG. Here, the convolutional neural network CNN2 preferably ascertains, by means of a confidence measure PK, whether a staining of kinetoplast regions is present for a minimum number of sub-image regions, preferably at least ten sub-image regions. If this is the case, the convolutional neural network CNN2 outputs the maximum brightness or the maximum brightness value, preferably 255, as the overall binding measure. If the convolutional neural network CNN2 establishes that the kinetoplast regions are not really stained, the fluorescence image SG is rated as overall negative.

Although some aspects have been described in connection with a device, it is self-evident that these aspects are also a description of the corresponding methods, and so a block or a component of a device is also to be understood as a corresponding method step or as a feature of a method step. Analogously, aspects which have been described in connection with a method step or as a method step are also a description of a corresponding block or detail or feature of a corresponding device.

Depending on specific implementation requirements, it is possible for exemplary embodiments of the invention to realize the computing unit R or the data network device in hardware and/or in software. A computing unit R mentioned here can be realized here as at least one computing unit or else by means of multiple computing units which are associated. Implementation can be effected using a digital storage medium, for example a floppy disc, a DVD, a Blu-Ray disc, a CD, a ROM, a PROM, an EPROM, an EEPROM or a FLASH memory, a hard drive or some other magnetic or optical storage device, which stores electronically readable control signals which interact or can interact with a programmable hardware component such that the respective method is carried out.

As computing unit, a programmable hardware component can be formed by a processor, a central processing unit (CPU), a computer, a computer system, an application-specific integrated circuit (ASIC), an integrated circuit (IC), a system on chip (SOC), a programmable logic element or a field programmable gate array with a microprocessor (FPGA).

The digital storage medium can therefore be machine-readable or computer-readable. Some exemplary embodiments thus encompass a data carrier having electronically readable control signals capable of interacting with a programmable computer system or a programmable hardware component such that one of the methods described herein is carried out.

In general, exemplary embodiments or parts of the exemplary embodiments of the present invention can be implemented as a program, firmware, computer program or computer program product with a program code or as data, wherein the program code or the data is/are operative to the effect of carrying out one of the methods or a part of a method when the program runs on a processor or a programmable hardware component.

What is claimed is:

1. A method for detecting a binding of autoantibodies from a patient sample to double-stranded deoxyribonucleic acid using *Crithidia luciliae* cells by means of fluorescence microscopy and by means of digital image processing, the method comprising:
    provision of a substrate which has multiple *Crithidia luciliae* cells;
    incubation of the substrate with the patient sample which potentially has the autoantibodies;
    incubation of the substrate with secondary antibodies which have each been labelled with a green fluorescent dye;
    acquisition of a fluorescence image of the substrate in a green color channel which corresponds to the fluorescent dye;
    identification by means of a first pretrained convolutional neural network of respective sub-images in the one fluorescence image that each represent a *Crithidia luciliae* cell;
    respective processing of at least one subset of the respective sub-images by means of a second pretrained convolutional neural network for determining respective binding measures which indicate a respective extent of a binding of autoantibodies in a respective kinetoplast region of a respective *Crithidia luciliae* cell of a respective sub-image; and
    determination of an overall binding measure with regard to the binding of autoantibodies from the patient sample to double-stranded deoxyribonucleic acid on the basis of the respective binding measures.

2. The method according to claim 1, wherein:
    the identification of the respective sub-images in the one fluorescence image is effected by assigning respective image segments of the fluorescence image to respective image segment classes from a group of image segment classes by means of the first pretrained convolutional neural network; and
    the group of the image segment classes comprises at least the following image segment classes: cell and background.

3. The method according to claim 1, wherein:
    the identification of the respective sub-images in the one fluorescence image is effected by assigning respective image segments of the fluorescence image to respective image segment classes from a group of image segment classes by means of the first pretrained convolutional neural network; and
    the group of the image segment classes comprises at least the following image segment classes: cell body, cell edge and background.

4. The method according to claim 1 further comprising:
    for a respective sub-image:
        selection of a respective subordinate image of the respective sub-image,
        wherein the respective subordinate image represents a respective kinetoplast region of a respective *Crithidia luciliae* cell; and
        determination of the respective binding measure on the basis of the respective subordinate image; and
    determination of the overall binding measure on the basis of the respective binding measures.

5. The method according to claim 1 further comprising:
    determination of a respective final feature map for a respective sub-image by means of the second convolutional neural network;
    determination of a respective confidence measure with regard to a presence of a binding of autoantibodies in a respective kinetoplast region for the respective sub-image;
    selection of a subset of the sub-images on the basis of the determined confidence measures;
    respective processing of the respective feature maps of the respective selected sub-images for determining the respective binding measures; and
    determination of the overall binding measure on the basis of the respective binding measures of the respective selected sub-images.

6. The method according to claim 5 further comprising:
    for a respective sub-image from the selected subset:
        selection of a respective subordinate image of the respective sub-image on the basis of a respective final feature map corresponding to the respective sub-image,
        wherein the respective subordinate image represents a respective kinetoplast region of a respective *Crithidia luciliae* cell; and
        determination of the respective binding measure on the basis of the respective subordinate image; and
    determination of the overall binding measure on the basis of the respective binding measures.

7. The method according to claim 6 further comprising:
    for a respective sub-image from the selected subset:
        ascertainment of a respective masking operator on the basis of the respective final feature map;
        selection of the respective subordinate image of the respective sub-image by means of application of the respective masking operator to the respective sub-image; and
        determination of the respective binding measure on the basis of the respective subordinate image; and
    determination of the overall binding measure on the basis of the respective binding measures.

8. The method according to claim 5, wherein, in the course of a processing of a sub-image, the second convolutional neural network:
    in a first processing level, generates a first set of resultant feature maps on the basis of the sub-image by means of at least one first convolutional layer and by means of application of multiple two-dimensional convolution kernels; and
    in a second processing level:
        generates a second set of resultant feature maps on the basis of the first set of two-dimensional feature maps by means of at least one second convolutional layer and by means of application of multiple three-dimensional convolution kernels; and
    generates a third set of resultant feature maps on the basis of the second set of two-dimensional feature maps by means of at least one third convolutional layer and by means of application of multiple three-dimensional convolution kernels, wherein the second set has a smaller number of resultant feature maps than the first set, and wherein the third set has a larger number of resultant feature maps than the second set.

9. The method according to claim 8, wherein:

in the second processing level:
the second convolutional layer and the third convolutional layer are in a sequence as sub-steps of a sequential processing path; and there is in parallel to the sequential processing path a further processing path in which the second convolutional neural network generates a fourth set of resultant feature maps on the basis of the first set of two-dimensional feature maps by means of at least one fourth convolutional layer;

the second convolutional neural network generates, on the basis of the third and fourth set of resultant feature maps, the final feature map corresponding to the sub-image; and the number of successive convolution layers in the parallel processing path is smaller than the number of successive convolution layers in the sequential processing path.

10. The method according to claim 1, further comprising:

acquisition of a first preliminary fluorescence image in the color channel using a predefined acquisition parameter;

establishment of whether a brightness of the first preliminary fluorescence image of the color channel exceeds a maximum brightness;

in the event of the first preliminary fluorescence image of the color channel not exceeding the maximum brightness, use of the first preliminary fluorescence image as the one fluorescence image; and in the event of the first preliminary fluorescence image of the color channel exceeding the maximum brightness, acquisition of a second preliminary fluorescence image in the color channel and use of the second preliminary fluorescence image of the color channel as the one fluorescence image.

11. A device for detecting a binding of autoantibodies from a patient sample to double-stranded deoxyribonucleic acid using *Crithidia luciliae* cells by means of fluorescence microscopy and by means of digital image processing, the device comprising:

a mounting device for a substrate which has multiple *Crithidia luciliae* cells and which has been incubated with a patient sample having the autoantibodies and, furthermore, with secondary antibodies which have each been labelled with a green fluorescent dye;

at least one image acquisition unit for acquiring a fluorescence image of the substrate in a green color channel which corresponds to the fluorescent dye; and at least one computing unit which is configured to:
identify by means of a first pretrained convolutional neural network respective sub-images in the one fluorescence image that each represent at least one *Crithidia luciliae* cell;

respectively process at least one subset of the respective sub-images by means of a second pretrained convolutional neural network for determining respective binding measures which indicate a respective extent of a binding of autoantibodies in a respective kinetoplast region of a respective *Crithidia luciliae* cell of a respective sub-image; and determine an overall binding measure of a binding of autoantibodies from the patient sample to double-stranded deoxyribonucleic acid on the basis of the respective binding measures.

12. A computing unit configured, in the course of a digital image processing, to:

receive a fluorescence image which represents a staining of a substrate, which in turn has multiple *Crithidia luciliae* cells, by a green fluorescent dye;

identify by means of a first pretrained convolutional neural network respective sub-images in the one fluorescence image that each represent at least one *Crithidia luciliae* cell;

respectively process at least one subset of the respective sub-images by means of a second pretrained convolutional neural network for determining respective binding measures which indicate a respective extent of a binding of autoantibodies in a respective kinetoplast region of a respective *Crithidia luciliae* cell of a respective sub-image; and determine an overall binding measure of a binding of autoantibodies from the patient sample to double-stranded deoxyribonucleic acid on the basis of the respective binding measures.

13. A data network device comprising:

at least one data interface for receiving a fluorescence image which represents a staining of a substrate, which in turn has multiple *Crithidia luciliae* cells, by a green fluorescent dye; and at least one computing unit configured, in the course of a digital image processing, to:
identify by means of a first pretrained convolutional neural network respective sub-images in the one fluorescence image that each represent at least one *Crithidia luciliae* cell;

respectively process at least one subset of the respective sub-images by means of a second pretrained convolutional neural network for determining respective binding measures which indicate a respective extent of a binding of autoantibodies in a respective kinetoplast region of a respective *Crithidia luciliae* cell of a respective sub-image; and determine an overall binding measure of a binding of autoantibodies from the patient sample to double-stranded deoxyribonucleic acid on the basis of the respective binding measures.

14. A method for digital image processing, comprising:

receiving of a fluorescence image which represents a staining of a substrate, which in turn has multiple *Crithidia luciliae* cells, by a green fluorescent dye;

identification by means of a first pretrained convolutional neural network of respective sub-images in the fluorescence image that each represent a *Crithidia luciliae* cell;

respective processing of at least one subset of the respective sub-images by means of a second pretrained convolutional neural network for determining respective binding measures which indicate a respective extent of a binding of autoantibodies in a respective kinetoplast region of a respective *Crithidia luciliae* cell of a respective sub-image; and determination of an overall binding measure of a binding of autoantibodies from the patient sample to double-stranded deoxyribonucleic acid on the basis of the respective binding measures.

* * * * *